US008551745B2

(12) United States Patent
Sasaki et al.

(10) Patent No.: US 8,551,745 B2
(45) Date of Patent: Oct. 8, 2013

(54) METHOD OF PRODUCING LACTIC ACID BY CONTINUOUS FERMENTATION

(75) Inventors: Nanami Sasaki, Kamakura (JP); Ken Morita, Kamakura (JP); Takashi Mimitsuka, Kamakura (JP); Hideki Sawai, Kamakura (JP); Katsushige Yamada, Kamakura (JP)

(73) Assignee: Toray Industries, Inc. (JP)

( * ) Notice: Subject to any disclaimer, the term of this patent is extended or adjusted under 35 U.S.C. 154(b) by 329 days.

(21) Appl. No.: 12/865,934

(22) PCT Filed: Feb. 3, 2009

(86) PCT No.: PCT/JP2009/051750
§ 371 (c)(1),
(2), (4) Date: Aug. 6, 2010

(87) PCT Pub. No.: WO2009/099044
PCT Pub. Date: Aug. 13, 2009

(65) Prior Publication Data
US 2011/0053231 A1    Mar. 3, 2011

(30) Foreign Application Priority Data

Feb. 4, 2008  (JP) ................................ 2008-023917
Feb. 15, 2008  (JP) ................................ 2008-034462

(51) Int. Cl.
*C12P 7/56*    (2006.01)

(52) U.S. Cl.
USPC ............................. 435/139; 435/183; 435/41

(58) Field of Classification Search
USPC ........................... 435/139, 41, 183
See application file for complete search history.

(56) References Cited

U.S. PATENT DOCUMENTS

| 5,776,526 | A | 7/1998 | Baensch et al. |
| 6,268,189 | B1* | 7/2001 | Skory ........................... 435/139 |
| 6,429,006 | B1* | 8/2002 | Porro et al. ................ 435/254.2 |
| 2003/0150808 | A1 | 8/2003 | Morikawa et al. |
| 2005/0112737 | A1 | 5/2005 | Liu et al. |
| 2007/0161098 | A1 | 7/2007 | Yamaguchi et al. |
| 2009/0239274 | A1 | 9/2009 | Sawai et al. |
| 2009/0269812 | A1 | 10/2009 | Sawai et al. |
| 2010/0190222 | A1 | 7/2010 | Ito et al. |

FOREIGN PATENT DOCUMENTS

| JP | 62-138184 A | 6/1987 |
| JP | 5-095778 A | 4/1993 |
| JP | 10-174594 A | 6/1998 |
| JP | 2000-139326 A | 5/2000 |
| JP | 2001-204464 A | 7/2001 |
| JP | 2002-027974 A | 1/2002 |
| JP | 2002-253212 A | 9/2002 |
| JP | 2003-259878 A | 9/2003 |
| JP | 2005-333886 A | 12/2005 |
| JP | 2006-006271 A | 1/2006 |
| JP | 2006-020602 A | 1/2006 |
| JP | 2006-075133 A | 3/2006 |
| JP | 2007-089466 A | 4/2007 |
| JP | 2007-252367 A | 10/2007 |
| JP | 2008-035727 A | 2/2008 |
| JP | 2008-048726 A | 3/2008 |
| WO | 02/064240 A1 | 8/2002 |
| WO | 2007/043253 A1 | 4/2007 |
| WO | 2007/097260 A1 | 8/2007 |
| WO | 2009/004922 A1 | 1/2009 |

OTHER PUBLICATIONS

Danilo Porro et al., "Development of Metabolically Engineered *Saccharomyces cerevisiae* Cells for the Production of Lactic Acid," Biotechnology Progress, vol. 11, No. 3, 1995, pp. 294-298.

Eri Adachi et al., "Modification of Metabolic Pathways of *Saccharomyces cerevisiae* by the Expression of Lactate Dehydrogenase and Deletion of Pyruvate Decarboxylase Genes for the Lactic Acid Fermentation at Low pH Value," Journal of Fermentation and BioEngineering, vol. 86, No. 3, 1998, pp. 284-289.

Nobuhiro Ishida et al., "Efficient Production of $_L$-Lactic Acid by Metabolically Engineered *Saccharomyces cerevisiae* with a Genome-Integrated $_L$-Lactate Dehydrogenase Gene," Applied and Environmental Microbiology, vol. 71, No. 4, Apr. 2005, pp. 1964-1970.

Miho Kawahata et al., "Yeast genes involved in response to lactic acid and acetic acid: acidic conditions caused by the organic acids in *Saccharomyces cerevisiae* cultures induce expression of intracellular metal metabolism genes regulated by Aft1p," FEMS Yeast Res., vol. 6, 2006, pp. 924-936.

Sugiyama, M. et al., "Breeding of L-Latic Acid Tolerant Strains of *Saccharomyces cerevisiae* by Multiple Gene Disruptions," *Abstracts of the Annual Meeting of the Society for Biotechnology, Japan*, vol. 58, p. 135, IHI6-3, one sheet in Japanese and one sheet of English translation.

* cited by examiner

*Primary Examiner* — Susan Hanley
*Assistant Examiner* — Nghi Nguyen
(74) *Attorney, Agent, or Firm* — DLA Piper LLP (US)

(57) ABSTRACT

A method of producing lactic acid continuous fermentation including filtering a culture of polyploid yeast having a capacity to produce lactic acid through a porous membrane having an average pore size of not less than 0.01 μm and less than 1 μm, and recovering the product from the filtrate while the unfiltered liquid is retained in or returned to the culture and a fermentation feedstock is added to the culture.

7 Claims, 6 Drawing Sheets

SEQUENCE LISTING

<160> NUMBER OF SEQ ID NOS: 28

<210> SEQ ID NO 1
<211> LENGTH: 999
<212> TYPE: DNA
<213> ORGANISM: Xenopus laevis

<400> SEQUENCE: 1

```
atggcaactg tgaaggataa actcatccac aatgtggtca aggaggagtc gctcccccag    60
aacaaggtca ccattgtggg tgtgggggcc gtgggcatgg cctgtgccat cagtgtcctg   120
cagaaggatt tggcagatga gcttgcactt gttgatgtga tagaagacaa actgaagggg   180
gaaatgatgg atctccagca tggcagtctg ttccttcgta cccccaagat tgtctcaggg   240
aaagattaca gcgtcactgc aaactccaag ctggtagttg tgacggccgg ggcccgtcag   300
caggagggag agagtcgcct gaatctggtt cagcgcaatg tcaacatctt caaattcatc   360
attcccaaca ttgtcaagta cagcccccaac tgcaccctgc tcatcgtctc caacccagtg   420
gacattctga catatgtggc ctggaagatc agtggattcc ccaaaaaccg tgtcattggc   480
agcggctgca atttggactc tgcccgtttc cgttacctca tggggcagaa gtttgggatc   540
cacacccaga gctgccacgg ttgggtcatt ggggaacacg gagactcgag tgtgccagtg   600
tggagtgggg tgaatgtggc tggcgtgtcc ctgaaaaccc tgcaccccga tattgggagt   660
gacgcagaca aggagaactg gaaggaggtg cacaagcagg ttgtggacag cgcctatgaa   720
gtgatcaagc tgaagggcta cacctcctgg gctattggcc tgtccgtagc tgacctgtct   780
gagagtatcc tgaagaacct ccgccgagtc catcccattt ccacaatggt caagggcatg   840
tacggcgtga ataatgatgt tttcctcagt gtccctgtg tgttgggcaa cttgggcatc    900
acagacgtgg ttaacatgac gctgaaggca gatgaagagg atcgcttacg caagagcgca   960
gacaccctgt gggccatcca gaaggagctg cagttctag                          999
```

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2

```
gtcgacatgg caactgtgaa ggataa                                          26
```

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3

```
gcggccgcct agaactgcag ctcctt                                          26
```

```
<210> SEQ ID NO 4
<211> LENGTH: 85
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tctcaattat tattttctac tcataacctc acgcaaaata acacagtcaa atcaatcaaa        60
atggcaactg tgaaggataa actca                                              85

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aggcgtatca cgaggccctt                                                    20

<210> SEQ ID NO 6
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gaattaattc ttgaagacga aagggcctcg tgatacgcct agattgtact gagagtgcac        60

<210> SEQ ID NO 7
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7 tattttt cgt tacataaaaa tgcttataaa actttaacta ataattagag attaaatcgc        60
ctgtgcggta tttcacaccg                                                    80

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
caaatatcgt tgaatatttt ttccg                                              25

<210> SEQ ID NO 9
<211> LENGTH: 85
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tattgattta tagtcgtaac tacaaagaca agcaaaataa aatacgttcg ctctattaag        60
```
atggcaactg tgaaggataa actca                                          85

<210> SEQ ID NO 10
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aaaaaataac ataatactga aagaaagcat taagaaggcg gatgtgtcaa acaccaccgt    60
ctgtgcggta tttcacaccg                                                80

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tagattggcc gtagggctg                                                 20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cacgcaacgc gtaagaaaca                                                20

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gcggccgcga atttcttatg atttat                                         26

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aagcttaagc ttgcatgccg gtagag                                         26

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15

```
aggcgtatca cgaggccctt                                              20

<210> SEQ ID NO 16
<211> LENGTH: 85
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tttttttagt tttaaaacac caagaactta gtttcgaata acacacata aacaaacaaa    60 atggcaactg tgaaggataa actca                                        85

<210> SEQ ID NO 17
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gaattaattc ttgaagacga aagggcctcg tgatacgcct agattgtact gagagtgcac   60

<210> SEQ ID NO 18
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ctaagtcata aagctataaa aagaaaattt atttaaatgc aagatttaaa gtaaattcac   60
ctgtgcggta tttcacaccg                                              80

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
atttcttaaa cttcttaaat tctac                                        25

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
atgaatcgaa aatgtcatta aaata                                        25

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 21
gacaattctg gttaggtcca agag                                              24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ttaagctgct gcggagcttc cacg                                              24

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
atgtctgccc ctaagaagat cg                                                22

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ttaagcaagg attttcttaa cttc                                              24

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
atggattcta gaavagttgg tata                                              24

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ttacttgttt tctagataag cttc                                              24

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
```

-continued

```
atgtcgaaag ctacatataa gcaa                                          24

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ttattttgct ggccgcatct tct                                           23
```

METHOD OF PRODUCING LACTIC ACID BY CONTINUOUS FERMENTATION

RELATED APPLICATIONS

This is a §371 of International Application No. PCT/JP2009/051750, with an international filing date of Feb. 3, 2009 (WO 2009/099044 A1, published Aug. 13, 2009), which is based on Japanese Patent Application Nos. 2008-023917, filed Feb. 4, 2008, and 2008-034462, filed Feb. 15, 2008, the subject matter of which is incorporated by reference.

SEQUENCE LISTING

The instant application contains a Sequence Listing which has been submitted via EFS-Web and is hereby incorporated by reference in its entirety. Said ASCII copy, created on Aug. 17, 2010, is named TOR10127.txt and is 8.417 bytes in size.

TECHNICAL FIELD

This disclosure relates to a method for producing lactic acid by continuous fermentation, wherein polyploid yeast having a capacity to produce lactic acid is employed to stabilize culturing of and fermentation by the yeast, thereby enabling long-term efficient production of lactic acid.

BACKGROUND

Methods of fermentation can be largely classified into Batch fermentation and Fed-Batch fermentation, and continuous fermentation. Batch fermentation and Fed-Batch fermentation can be carried out with a simple equipment and finished in a short time, and is therefore less prone to be suffered from contamination, which is advantageous. However, there is a problem in that, as the product concentration in the culture increases with time, the productivity and the yield decrease due to the influence(s) of the osmotic pressure, product inhibition and/or the like. Therefore, it is difficult to maintain the stability, a high yield and a high productivity for a long time. Continuous fermentation has an advantage in that accumulation of a desired substance in the fermenter at a high concentration can be avoided and thereby a high yield and a high productivity can be maintained for a long time, but it is very difficult to stably continue culture by continuous fermentation for a long time, so that researches have been carried out therefor.

As a proposal for continuous fermentation, there is a method wherein microorganisms or cultured cells are filtered through a separation membrane and the product is recovered from the filtrate, while the microorganisms or cultured cells which were subjected to the filtration are retained in or returned to the culture to maintain a high concentration of the microorganisms or cultured cells in the culture.

For example, technologies wherein continuous fermentation is carried out in a continuous fermentation device having a ceramic membrane are disclosed (JP 5-95778 A, JP 62-138184 A, JP 10-174594 A and JP 2005-333886 A). However, the disclosed technologies have problems of decreases in the filtration flow rate and the filtration efficiency due to clogging of the ceramic membrane, so that reverse washing or the like is carried out to prevent the clogging.

A method for producing succinic acid by continuous fermentation (JP 2007-252367 A) is also disclosed. In this technology, a high filtration pressure (about 200 kPa) is employed for membrane separation. Since a high filtration pressure is disadvantageous in terms of not only the cost but also physical damage to microorganisms or cells by the pressure during filtration, it is inappropriate for continuous fermentation wherein microorganisms or cells are continuously returned to the culture. In JP 2007-252367 A, as proposals for maintaining continuous fermentation for a long time, technologies for the separation membrane, the filtration pressure and the like are disclosed, but the length of time of the continuous fermentation is about 300 hours, and therefore a method to maintain continuous culture for a longer period of time is demanded.

On the other hand, studies on microorganisms to be used for producing organic acids have been intensively carried out employing yeasts having high tolerances for acids (Biotechnology Progress, 11, 294-298 (1995) and Journal of Fermentation and Bioengineering, 86, 284-289 (1998)). In yeasts, there are haploid yeasts having only single sets of chromosomes and polyploid yeasts having pluralities of sets of chromosomes. Polyploid yeasts are used mainly as baker's yeasts and brewer's yeasts (JP 2000-139326 A, JP 2002-027974 A and JP 2002-253212 A). These are used for production of foods and beverages for the purposes of enhancement of flavor and improvement of the production process, and there is no description of their usage for continuous culture.

Further, methods for producing lactic acid using polyploids are disclosed (JP 2006-006271 A, JP 2006-020602 A, JP 2007-089466 A and JP 2001-204464 A). These employ polyploids to increase the number of the lactic acid synthetic gene, but the culture is carried out by Fed-Batch fermentation and the culturing time is as short as not more than 100 hours, and there is no description of continuous fermentation using a membrane.

In addition, production of lactic acid using prototrophic yeast which does not show auxotrophy was reported (US 2005/0112737 A), but also in this case, the culturing time is less than 100 hours, and Fed-Batch fermentation is the only method disclosed as a fermentation method.

Thus, continuous fermentation to enhance the productivity, and the microorganism to be used for fermentation have been separately studied. In cases where microorganisms were cultured by continuous fermentation which is advantageous as a fermentation method, the filtration pressure increased during the culture and continuation of the culture for a long time became impossible or the productivity of lactic acid decreased as the culture was continued longer, so that it has so far been difficult to allow exertion of the both advantages sufficiently. Thus, development of a technology for continuous fermentation which solves these problems and allows stable production of lactic acid for a long time has been demanded.

It could therefore be helpful to provide a method for production of lactic acid by continuous fermentation, by which a high productivity of lactic acid can be stably maintained for a long time.

SUMMARY

We discovered that, to allow lactic acid-producing yeast to maintain a high productivity of lactic acid while stably repeating their proliferation for a long time during continuous fermentation, maintenance of the high productivity of lactic acid for a long time can be achieved by employing polyploid yeast having lactic acid-producing capacity.

We thus provide:
(1) A method for producing lactic acid by continuous fermentation, wherein culture of polyploid yeast having a capacity to produce lactic acid is filtered through a porous membrane having an average pore size of not less than 0.01 μm and less than 1 μm and the product is recovered from the filtrate, while the unfiltered liquid is retained in or returned to the culture and a fermentation feedstock is added to the culture.

(2) The method for producing lactic acid according to (1), wherein said filtration is carried out with a transmembrane pressure difference of the porous membrane within the range of 0.1 kPa to less than 20 kPa.

(3) The method for producing lactic acid according to (1) or (2), wherein the polyploid yeast is diploid.

(4) The method for producing lactic acid according to any one of (1) to (3), wherein the polyploid yeast is prototrophic.

(5) The method for producing lactic acid according to any one of (1) to (4), wherein the yield of lactic acid to saccharides in the continuous fermentation is not less than 70%.

(6) The method for producing lactic acid according to any one of (1) to (5), wherein the concentration of accumulated lactic acid in the culture subjected to the continuous fermentation is not less than 40 g/L.

(7) The method for producing lactic acid according to any one of (1) to (6), wherein the rate of production of lactic acid during the continuous fermentation is not less than 7.5 g/L/h.

(8) The method for producing lactic acid according to any one of (5) to (7), wherein the continuous fermentation is continued for not less than 400 hours.

(9) The method for producing lactic acid according to any one of (1) to (8), wherein the polyploid yeast belongs to Saccharomyces.

(10) The method for producing lactic acid according to any one of (1) to (9), wherein the polyploid yeast is Saccharomyces cerevisiae.

By using polyploid yeast, continuous fermentation is possible which allows stable maintenance of a high productivity of lactic acid as the desired fermentation product for a long time, thereby enabling stable production of lactic acid at a low cost.

DESCRIPTION OF SYMBOLS

Figure 1:
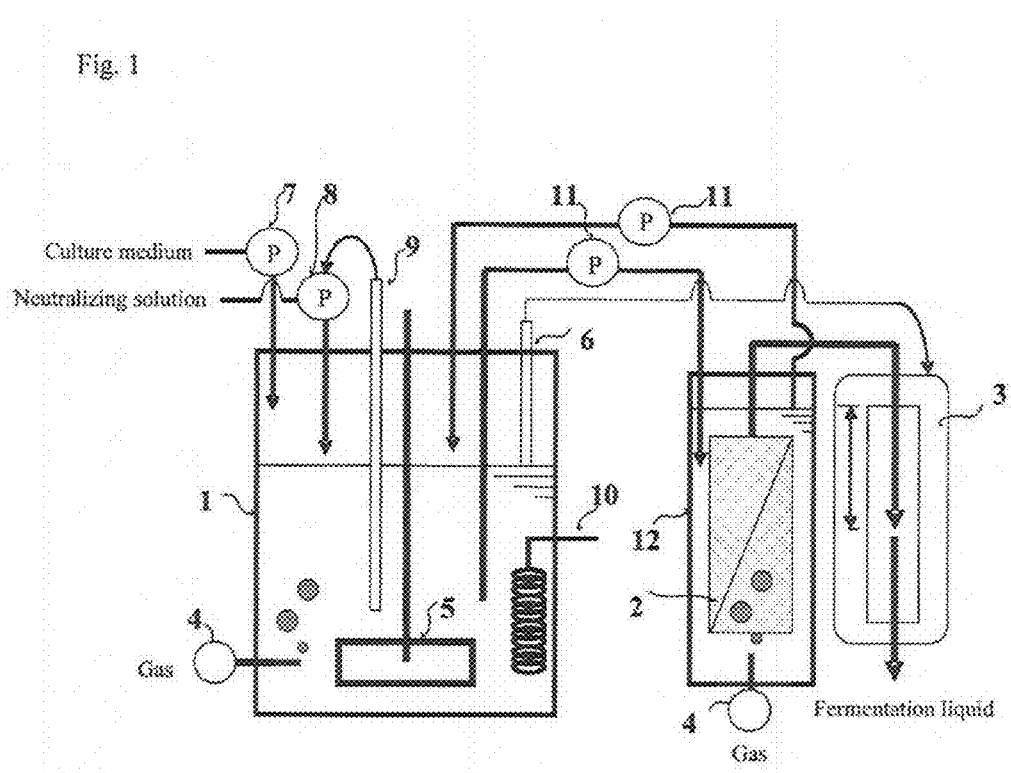
FIG. 1 is a schematic side view for explanation of a continuous fermentation device of the membrane separation type.

1. Fermentation reaction vessel
2. Separation membrane element
3. Hydraulic head difference controlling apparatus
4. Gas supplying apparatus
5. Stirrer
6. Level sensor
7. Culture medium supplying pump
8. pH adjustment solution supplying pump
9. pH sensor/controlling apparatus
10. Temperature controller
11. Fermentation liquid circulating pump
12. Membrane separation vessel
13. Supporting plate
14. Channel material
15. Separation membrane
16. Recess
17. Liquid collection pipe
18. Separation membrane bundle
19. Upper resin sealing layer
20. Lower resin sealing layer
21. Support frame
22. Liquid collection pipe

DETAILED DESCRIPTION

We provide a method for producing lactic acid by continuous fermentation while, in fermentation by culturing yeast having a capacity to produce lactic acid, maintaining a high productivity of lactic acid for a long time by using polyploid yeast, wherein, during the continuous fermentation, culture of the polyploid yeast having a capacity to produce lactic acid is filtered through a separation membrane and the product is recovered from the filtrate, while allowing the unfiltered liquid to be retained in or returned to the culture and adding a fermentation feedstock to the culture, which separation membrane has an average pore size of not less than 0.01 μm and less than 1 μm.

First, the porous membrane as a separation membrane will be described. The porous membrane preferably has a separation performance and a permeability depending on the properties and the use of the liquid to be processed. The porous membrane preferably has a porous resin layer in view of the blocking performance, permeability and separation performance, for example, resistance to dirt.

The porous membrane comprising a porous resin layer preferably has a porous resin layer on the surface of a porous base material, which layer acts as a separation function layer. The material of the porous base material comprises an organic material, inorganic material and/or the like, and preferably an organic material, more preferably an organic fiber is used. Examples of the porous base material preferred among these include woven fabrics and non-woven fabrics using organic fibers such as cellulose fibers, cellulose triacetate fibers, polyester fibers, polypropylene fibers and polyethylene fibers, and a non-woven fabric whose density can be relatively easily controlled, whose production is easy and which is inexpensive is more preferably used. The thickness of the porous base material is preferably not less than 50 μm and not more than 3,000 μm in view of supporting the porous resin layer and strengthening the separation membrane. The porous base material may be either impregnated with the porous resin layer or not impregnated with the porous resin layer, which is selected depending on the use.

As the porous resin layer, an organic polymer membrane may be suitably used. Examples of the material of the organic polymer membrane include polyethylene resins, polypropylene resins, polyvinyl chloride resins, polyvinylidene fluoride resins, polysulfone resins, polyethersulfone resins, polyacrylonitrile resins, polyolefin resins, cellulose resins and cellulose triacetate resins, and the material may be a mixture of resins containing these resins as the major component. The major component means that the component is contained in an amount of not less than 50% by weight, preferably not less than 60% by weight. Preferred examples of the material of the organic polymer membrane especially include those which can be easily formed by a solution and are excellent in physical durability and chemical resistance, such as polyvinyl chloride resins, polyvinylidene fluoride resins, polysulfone resins, polyethersulfone resins, polyacrylonitrile resins and polyolefin resins, and mixtures of resins containing these resins as the major component. A polyvinylidene fluoride resin or a mixture of resins containing it as the major component is more preferably used.

As the polyvinylidene fluoride resin, a homopolymer of vinylidene fluoride or a copolymer with vinyl monomers capable of copolymerizing with vinylidene fluoride is preferably used. Examples of the vinyl monomers capable of copolymerizing with vinylidene fluoride include tetrafluoroethylene, hexafluoropropylene and chlorotrifluoroethylene.

Examples of the polyolefin resins include polyethylene, polypropylene, chlorinated polyethylene and chlorinated polypropylene, and chlorinated polyethylene is preferably used.

It is important for the porous membrane to have an average surface pore size of not less than 0.01 μm. With an average surface pore size of the porous membrane of not less than 0.01 μm, the membrane is less prone to clogging by the yeast cells used for the fermentation, and has a property to stably maintain the filtration performance for a long time. Further, with an average pore size of the porous membrane of not less than 0.01 μm, both a high blocking performance which does not allow leakage of the polyploid yeasts and a high permeability can be achieved, and the permeability can be maintained with high accuracy and reproducibility for a long time. In cases where the average surface pore size of the porous membrane is less than 0.01 μm, the permeability of the porous membrane decreases, and in some cases, efficient operation is impossible even if the membrane is not dirty. In cases where the average pore size of the porous membrane is not less than 0.01 μm, preferably not less than 0.02 μm, more preferably not less than 0.04 μm, efficient operation is possible.

It is important for the porous membrane to have an average pore size of less than 1 μm, preferably less than 0.4 μm, more preferably less than 0.2 μm to prevent leakage of the polyploid yeast, that is, occurrence of a trouble decreasing the elimination rate, and to prevent direct clogging of the pores by the polyploid yeast. Further, in some cases, the polyploid yeast produces substances other than lactic acid which is the substance of interest, such as proteins and saccharides that are prone to aggregation, and there are also cases where cell debris is produced by death of a part of the polyploid yeast in the culture. Therefore, to avoid clogging of the porous membrane by such substances, the average pore size of not more than 0.1 μm is more preferred. Thus, the average surface pore size of the porous membrane is preferably not more than 0.4 μm, more preferably not more than 0.2 μm, especially preferably not more than 0.1 μm.

The average surface pore size can be determined by observing the surface of the porous membrane with a scanning electron microscope at a magnification of 10,000× to measure the diameters of all the pores observable within an area of 9.2 μm×10.4 μm and calculating the average of the diameters. Alternatively, the average pore size can be determined by a method wherein a picture of the surface of the membrane is taken using a scanning electron microscope at a magnification of 10,000×, and not less than 10, preferably not less than 20 pores are randomly selected, followed by measuring the diameters of these pores and calculating the number average. In cases where a pore is not circular, the average pore size can be determined by a method wherein a circle having the area equal to that of the pore (equivalent circle) is determined using an image processing device or the like, and the diameter of the equivalent circle is regarded as the diameter of the pore.

In terms of the average surface pore size of the porous membrane, in cases where the standard deviation of the pore sizes is small, that is, in cases where the pore sizes are uniform, a uniform permeated liquid is more likely to be obtained, and the standard deviation σ is preferably not more than 0.1 μm. Further, in view of ease of management of fermentation operation, the standard deviation of the average pore size is preferably as small as possible. The standard deviation σ of the average pore size is calculated according to (Equation 1) below wherein N represents the number of pores observable within an area of 9.2 μm×10.4 μm under the above-mentioned observation of the surface of the porous membrane with a scanning electron microscope at a magnification of 10,000×, Xk represents the respective diameters observed, and X(ave) represents the average of the pore sizes:

$$\sigma = \sqrt{\frac{\sum_{k=1}^{N}(X_k - X(ave))^2}{N}}.$$ (Equation 1)

In the porous membrane, permeability to the culture is one of its important properties. As an index for permeability of the porous membrane, the pure water permeability coefficient of the porous membrane before use can be used. The pure water permeability coefficient of the porous membrane is preferably not less than $2\times10^{-9}$ m$^3$/m$^2$/s/pa when the amount of permeation is measured using, as the raw water, drinking water filtered through a dialysis membrane (Filtryzer B2-1.5H manufactured by Toray Industries, Inc.) at 25° C. with a head height of 1 m, and in cases where the pure water permeability coefficient is not less than $2\times10^{-9}$ m$^3$/m$^2$/s/pa and not more than $6\times10^{-7}$ m$^3$/m$^2$/s/pa, an amount of permeation of water which is practically sufficient can be obtained. More preferably, the pure water permeability coefficient is not less than $2\times10^{-9}$ m$^3$/m$^2$/s/pa and not more than $1\times10^{-7}$ m$^3$/m$^2$/s/pa.

The membrane surface roughness in the porous membrane is the average value of the heights from the surface in the vertical direction. The membrane surface roughness is one of the factors which enable easy detachment of polyploid yeast adhered to the surface of the separation membrane by the membrane surface washing effect of the liquid current produced by stirring or a circulating pump. The surface roughness of the porous membrane is preferably not more than 0.1 μm. In cases where the membrane surface roughness is not more than 0.1 μm, polyploid yeast adhered to the membrane can be easily detached and the shear force produced on the surface of the membrane can be reduced during filtration of the polyploid yeast. Therefore, destruction of the yeast is suppressed, and clogging of the porous membrane is also suppressed, so that stable filtration can be carried out for a long time, and, since the continuous fermentation can be carried out with a lower transmembrane pressure difference, even in cases where the membrane was clogged, a better washing recovery performance can be obtained compared to in cases where the operation was carried out with a higher transmembrane pressure difference. Since stable continuous fermentation is possible by suppressing clogging, the surface roughness of the porous membrane is preferably as small as possible.

The membrane surface roughness is measured using the following atomic force microscope (AFM) under the following conditions:
Device: Atomic Force Microscope (Nanoscope IIIa Manufactured by Digital Instruments)
    Conditions
    Probe: SiN cantilever (manufactured by Digital Instruments)
        Scanning mode Contact mode (measurement in air)
        Underwater tapping mode (measurement in water)
        Scanning area: 10 μm×10 μm, 25 μm×25 μm (measurement in air)
        5 μm×5 μm, 10 μm×10 μm (measurement in water)
        Scanning resolution: 512×512
        Sample preparation: When the measurement was carried out, the membrane sample was soaked in ethanol at room temperature for 15 minutes and then soaked in RO water for 24 hours, followed by washing and drying it in the air.

The membrane surface roughness (drough) is calculated according to the following (Equation 2) using the above atomic force microscope (AFM), based on the heights of respective points in the direction of the z-axis:

$$d_{rough} = \sum_{n=1}^{N} \frac{|Z_n - \bar{Z}|}{N} \qquad \text{(Equation 2)}$$

$d_{rough}$: Surface roughness (μm)
$Z_n$: Height in the direction of the z-axis (μm)
$\bar{Z}$: Average height in the scanned area (μm)
N: Number of samples measured.

The porous membrane may be either a flat membrane or a hollow fiber membrane. In cases where the porous membrane is a flat membrane, its average thickness is selected depending on the use thereof, and it is preferably not less than 20 μm and not more than 5,000 μm, more preferably not less than 50 μm and not more than 2,000 μm. In cases where the porous membrane is a hollow fiber membrane, the inner diameter of the hollow fiber is preferably not less than 200 μm and not more than 5,000 μm, and the membrane thickness is preferably not less than 20 μm and not more than 2000 μm. A fabric or a knit produced by forming an organic fiber or an inorganic fiber into a cylindrical shape may be contained in the hollow fiber.

The method for producing the porous membrane will be now described by way of examples.

First, a method for preparing a flat membrane which is one preferred embodiment of the porous membrane will now be described. On the surface of a porous base material, a coating of a starting solution containing a resin and a solvent is formed, while impregnating the starting solution into the porous base material. Thereafter, only the coated surface of the porous base material having the coating is brought into contact with a coagulation bath containing a nonsolvent to coagulate the resin, while forming a porous resin layer on the surface of the porous base material.

The starting solution is prepared by dissolving a resin into a solvent. The temperature of the starting solution is usually preferably selected within the range of 5 to 120° C. in view of the film-forming property. The solvent dissolves the resin and acts on the resin to promote formation of a porous resin layer by the resin. Examples of the solvent which may be used include N-methylpyrrolidinone (NMP), N,N-dimethylacetamide (DMAc), N,N-dimethylformamide (DMF), dimethylsulfoxide (DMSO), N-methyl-2-pyrrolidone, tetrahydrofuran, tetramethylurea, trimethyl phosphate, cyclohexanone, isophorone, γ-butyrolactone, methyl isoamyl ketone, dimethyl phthalate, propylene glycol methyl ether, propylene carbonate, diacetone alcohol, glycerol triacetate, acetone and methyl ethyl ketone. Among these, N-methylpyrrolidinone (NMP), N,N-dimethylacetamide (DMAc), N,N-dimethylformamide (DMF) and dimethyl-sulfoxide (DMSO), in which resins show high solubilities, can be preferably used. These may be used either individually or as a mixture of 2 or more thereof Further, a component(s) other than a solvent, such as polyethylene glycol, polyvinyl alcohol, polyvinylpyrrolidone and/or glycerin may be added to the solvent. A nonsolvent may also be added to the solvent. A nonsolvent is a liquid which does not dissolve a resin. The non-solvent has an action of regulating the rate of coagulation of a resin, thereby regulating the sizes of the pores. Examples of the nonsolvent which may be used include water and alcohols such as methanol and ethanol. Among these, water and methanol are preferred as the nonsolvent in view of the cost thereof. The compound other than a solvent, and the nonsolvent may be a mixture.

To the starting solution, a pore-forming agent may be added. The pore-forming agent is extracted upon immersion in the coagulation bath, thereby making the resin layer porous. Addition of a pore-forming agent allows the regulation of average pore size. The pore-forming agent preferably has a high solubility in the coagulation bath. Examples of the pore-forming agent include inorganic salts such as calcium chloride and calcium carbonate. Further examples of the pore-forming agent include polyoxyalkylenes such as polyethylene glycol and polypropylene glycol; water-soluble macromolecular compounds such as polyvinyl alcohol, polyvinyl butyral and polyacrylic acid; and glycerin.

The method of preparation of a hollow fiber membrane which is one preferred example of the porous membrane will now be described. A hollow fiber membrane can be prepared by extruding a starting solution comprising a resin and a solvent from the outer pipe of a double pipe mouthpiece, while extruding a fluid for formation of the hollow portion from the inner pipe, followed by cooling and solidifying the resultant in a cooling bath.

The starting solution can be prepared by dissolving the resin mentioned in the above-mentioned preparation method for a flat membrane in the solvent mentioned in the above-mentioned preparation method for a flat membrane at a concentration of not less than 20% by weight and not more than 60% by weight. As the fluid for formation of the hollow portion, a gas or a liquid can be usually used. Further, on the outer surface of the obtained hollow fiber membrane, another porous resin layer may be coated (laminated). The lamination may be carried out for changing properties of the hollow fiber membrane such as the hydrophilicity/hydrophobicity and the pore sizes to desired properties. The other porous resin layer to be laminated can be prepared by dissolving a resin in a solvent followed by bringing the resulting starting solution into contact with a coagulation bath containing a nonsolvent to coagulate the resin. Examples of the material of the resin which can be preferably used include ones similar to those of the material of the above-mentioned organic polymer membrane. The method of the lamination is not restricted, and examples thereof include immersion of the hollow fiber membrane in the starting solution and application of the starting solution to the surface of the hollow fiber membrane, and after the lamination, a part of the starting solution adhered may be scraped off or blown off with an air knife to adjust the the amount of lamination.

The porous membrane can be made into a separation membrane element by bonding and sealing the hollow portion of the hollow fiber membrane using a member such as a resin and placing the resultant on a support.

The porous membrane can be made into a separation membrane element by combining it with a support. A separation membrane element wherein a supporting plate is used as the support and the porous membrane is placed on at least one side of the supporting plate is one preferred form of the separation membrane element having the porous membrane. Placement of the porous membranes on the both sides of the supporting plate to increase the permeability is also a preferred example of the separation membrane element.

In the method for producing lactic acid, the filtration is preferably carried out with a transmembrane pressure difference of the porous membrane of not less than 0.1 kPa and less than 20 kPa. In cases where the filtration is carried out with a transmembrane pressure difference of not less than 20 kPa to filtrate the fermentation culture medium, power is necessary for applying the pressure and therefore the economic effect upon the production of lactic acid decreases. Further, by application of a higher transmembrane pressure difference of not less than 20 kPa, the polyploid yeast used in the continuous fermentation culture may be disrupted, leading to decrease in the capacity to produce lactic acid. With a transmembrane pressure difference of less than 0.1 kPa, the filtration takes time, leading to decrease in the production rate. Since in cases where the transmembrane pressure difference which is the filtration pressure is within the range of not less than 0.1 to less than 20 kPa, the transmembrane pressure difference can be obtained by the hydraulic head difference, so that the inside of the fermenter is not especially required to be kept pressured and the capacity to produce lactic acid does not decrease. Further, since the inside of the fermenter is not especially required to be kept pressurized, an embodiment wherein the porous membrane is placed inside the fermenter is possible, and hence the fermentation device can be downsized, which is advantageous.

The term "transmembrane pressure difference" herein means the pressure difference in the porous membrane between the side of the liquid to be processed and the side of the permeated liquid. When an operation is carried out at a constant processing flow rate per unit area of the porous membrane and the liquid to be processed is filtered through the porous membrane for a long time, pollutants existing in the liquid to be processed adhere to the pores on the porous membrane and accumulate on the surface, leading to pollution of the membrane. This causes clogging of the membrane and increases in the transmembrane pressure difference, leading to significant decrease in the processing flow rate and difficulty in continuation of a stable operation, so that the filtration is preferably carried out while measuring the transmembrane pressure difference. The transmembrane pressure difference can be measured by placing manometers in the sides of the liquid to be processed and the permeated liquid in the porous membrane and measuring the pressures, followed by calculating the pressure difference.

The polyploid yeast having a capacity to produce lactic acid will now be described. In the method for producing lactic acid, use of a polyploid yeast having a capacity to produce lactic acid enables, under simple operating conditions, continuous fermentation wherein a high productivity of lactic acid which is the desired fermentation product can be stably maintained for a long time, and therefore lactic acid can be stably produced at a low cost.

Polyploid yeast is yeast having 2 or more sets of chromosomes in the cell. Polyploid yeast is larger than haploid yeast generally used in genetic analyses, and therefore clogging of a porous membrane is not likely to occur, so that it is suitable for long-term culture. By using polyploid yeast, the shear force produced on the surface of the membrane can be reduced, destruction of the yeast is suppressed, and clogging of the porous membrane is also suppressed, so that stable filtration can be carried out for a long time, and moreover, since reuse of the membrane is possible, the cost can be reduced, which are advantageous. Further, even in cases where the membrane was clogged, a better washing recovery performance can be obtained compared to the cases of haploid yeast. The number of sets of chromosomes in the polyploid yeast is not restricted, and diploid yeast having 2 sets of chromosomes are preferred.

Examples of the polyploid yeast include yeasts such as baker's yeasts, sake yeasts, wine yeasts and beer yeasts frequently used in the fermentation industry. The polyploid yeast to be used may be isolated from a natural source or may be one whose properties were partially modified by mutation or genetic recombination.

Polyploid yeast having a capacity to produce lactic acid means polyploid yeast to which a lactate dehydrogenase gene (hereinafter also referred to as LDH) was introduced. The method of preparation of polyploid yeast to which a lactate dehydrogenase gene was introduced is not restricted, and polyploidization of haploid yeast to which a lactate dehydrogenase gene was introduced enables simple multiplication of the copy number of the lactate dehydrogenase gene without changing the genotypes per chromosome, eventually leading to enhancement of the lactic acid producing capacity.

Further, if the polyploid yeast having a capacity to produce lactic acid is prototrophic, a culture medium containing less nutrients than conventional media, that is, a low-cost culture medium can be employed, and continuous fermentation which allows stable maintenance of a high productivity of lactic acid for a long time is possible under simple operating conditions, enabling low-cost and stable production of lactic acid, so that prototrophic yeast is preferably used.

Auxotrophy of yeast means that a mutation occurred to a nutrient-synthesis gene in the wild type yeast, resulting in deficiency of the synthesis capacity of a nutrition. Reversion from auxotrophy means reversion of the auxotrophic mutation to the wild type or a state very similar thereto. Since auxotrophy is used as a marker for mainly genetic manipulation and the like, auxotrophic yeast is preferably used for genetic manipulation.

Known examples of nutrients necessary for yeast showing auxotrophy include methionine, tyrosine, isoleucine, phenylalanine, glutamic acid, threonine, aspartic acid, valine, serine, arginine, uracil, adenine, lysine, tryptophan, leucine and histidine. Examples of genotypes in yeast showing auxotrophy include the followings:

methionine auxotrophy: met1, met2, met3, met4, met5, met6, met7, met8, met10, met13, met14, met20;
tyrosine auxotrophy: tyr1;
isoleucine-valine auxotrophy: ilv1, ilv2, ilv3, ilv5;
phenylalanine auxotrophy: pha2;
glutamic acid auxotrophy: GLU3;
threonine auxotrophy: thr1, thr4;
aspartic acid auxotrophy: asp1, asp5;
serine auxotrophy: ser1, ser2;
arginine auxotrophy: arg1, arg3, arg4, arg5, arg8, arg9, arg80, arg81, arg82, arg84;
uracil auxotrophy: ura1, ura2, ura3, ura4, ura6;
adenine auxotrophy: ade1, ade2, ade3, ade4, ade5, ade6, ade8, ade9, ade12, ADE15;
lysine auxotrophy: lys1, lys2, lys4, lys5, lys7, lys9, lys11, lys13, lys14;
tryptophan auxotrophy: trp1, trp2, trp3, trp4, trp5;
leucine auxotrophy: leu1, leu2, leu3, leu4, leu5; and
histidine auxotrophy: his1, his2, his3, his4, his5, his6, his7, his8.

The prototrophic yeast preferably is yeast having no genotype showing the above-described auxotrophies or yeast wherein such a genotype is complemented. Whether or not yeast is prototrophic can be judged based on whether or not the yeast can be grown in SD medium (Table 1) which is a minimal medium for yeast.

TABLE 1

| YEAST NITROGEN W/O AA (manufactured by Difco) | 1.7 g |
|---|---|
| Glucose | 30 g |
| Agar | 20 g |
|  | up to 1 L |

Examples of the method for preparing a prototrophic yeast by reversion from the auxotrophy in an auxotrophic yeast include a method wherein a nutrient-synthesis gene is introduced by a gene recombination technique to allow reversion from the auxotrophy and a method wherein the process in which yeasts having different auxotrophies are mated with each other and ascus formation is allowed to occur, thereby allowing reversion from an auxotrophy of interest is repeated until completion of reversion from all the auxotrophies, to obtain a prototrophic yeast.

The LDH introduced in the polyploid yeast having a capacity to produce lactic acid is not restricted as long as it encodes a protein having an activity of converting reduced nicotinamide adenine dinucleotide (NADH) and pyruvic acid into oxidized nicotinamide adenine dinucleotide (NAD+) and lactic acid, and examples of the available LDH include LDHs derived from lactic acid bacteria having high yields of lactic acid to saccharides and LDHs derived from mammals and LDHs derived from amphibians. Among these, LDHs derived from *Homo sapiens* and frogs are preferably used. Among the frogs, LDHs derived from frogs belonging to Pipidae are preferably used, and among the frogs belonging to Pipidae, LDHs derived from *Xenopus laevis* can be preferably used.

The LDHs include genes having genetic polymorphisms and mutant-type genes produced by mutagenesis or the like. "Genetic polymorphism" means that a part of the base sequence of a gene is changed due to a natural mutation(s) on the gene, and "mutagenesis" means that a mutation(s) is/are artificially introduced to a gene. Examples of the method of mutagenesis include a method using a site-directed mutagenesis kit (Mutan-K (TAKARA BIO INC.)) and a method using a random mutagenesis kit (BD Diversify PCR Random Mutagenesis (CLONTECH)). The LDH may have a deletion(s) and/or an insertion(s) in a part of its base sequence as long as it encodes a protein having an activity of converting NADH and pyruvic acid into NAD+ and lactic acid.

In the polyploid yeast having a capacity to produce lactic acid, the LDH may be retained in a plasmid or YAC maintained outside the yeast chromosomes, but as mentioned above, it is preferably incorporated into a yeast chromosome and retained therein. The method of incorporation of a LDH into a yeast chromosome is not restricted and, for example, it may be introduced by a method disclosed in JP 2008-29329 A. In the polyploid yeast having a capacity to produce lactic acid, at least one, preferably not less than two, more preferably not less than three, still more preferably not less than 4 LDH(s) is/are retained.

The fermentation feedstock may be any fermentation feedstock as long as it promotes the growth of the yeast to be cultured and allows satisfactory production of lactic acid as the desired fermentation product, and examples thereof which are preferably used include liquid media containing carbon sources, nitrogen sources, inorganic salts and, if needed, organic micronutrients such as amino acids and vitamins as appropriate. Examples of the carbon sources which are preferably used include saccharides such as glucose, sucrose, fructose, galactose, lactose and maltose; saccharified starch solutions containing these saccharides; sweet potato molasses; sugar beet molasses; high test molasses; cane juices; extracts and concentrated liquids of cane juices; raw sugars purified or crystallized from cane juices; refined sugars purified or crystallized from cane juices; and further, organic acids such as acetic acid and fumaric acid; alcohols such as ethanol; and glycerin. The term "saccharide" means the first oxidation product of a polyol, which is a carbon hydrate having an aldehyde group or a ketone group, and one having an aldehyde group is classified as aldose and one having a ketone group is classified as ketose. It is preferably glucose, sucrose, fructose, galactose, lactose or maltose. The carbon source may be added at one time when the culture is begun or may be added intermittently or continuously during the culture.

Examples of the nitrogen source used include ammonia gas, aqueous ammonia, ammonium salts, urea and nitric acid salts; and other organic nitrogen sources used supplementarily such as oil cake, soybean-hydrolyzed liquids, casein digests, other amino acids, vitamins, corn steep liquors, yeasts or yeast extracts, meat extracts, peptides such as peptones, and various fermentation microorganisms and hydrolysates thereof.

Examples of the inorganic salt which may be added as appropriate include phosphoric acid salt, magnesium salt, calcium salt, iron salt and manganese salt.

In cases where the polyploid yeast having a capacity to produce lactic acid is auxotrophic, the nutrient may be added as a preparation or a natural product containing it. An antiforming agent may also be added as required.

The conditions of the fermentation culture of the polyploid yeast having a capacity to produce lactic acid are not restricted as long as the yeast can be cultured, and it is preferably carried out at a pH of 4 to 8 and a temperature of 20 to 40° C. The pH of the fermentation culture medium is adjusted to a value predetermined within the above-described range with an inorganic acid or organic acid; alkaline substance; urea; calcium carbonate; or ammonia gas.

During the fermentation culture of the polyploid yeast having a capacity to produce lactic acid, if the feed rate of oxygen is required to be increased, a method can be employed in which the oxygen concentration is maintained at not less than 21% by adding oxygen into the air; the pressure of the culture medium is increased; the stirring rate is increased; or the ventilation volume is increased. On the other hand, if the feed rate of oxygen is required to be decreased, a gas which does not contain oxygen, such as carbon dioxide gas, nitrogen or argon may be mixed with the air and supplied.

Batch fermentation or Fed-Batch fermentation may be carried out at the initial phase of the culture to increase the yeast cell concentration, followed by starting the continuous culture (withdrawal), or the yeast cells may be seeded at a high concentration and subjected to the continuous culture at the beginning of the culture. It is possible to start supplying the fermentation feedstock liquid and withdrawing the culture at an appropriate timing. The timing of the start of supplying of the fermentation feedstock liquid and the timing of the start of withdrawing of the culture are not necessarily the same. The supplying of the fermentation feedstock liquid and the withdrawing of the culture may be carried out either continuously or intermittently. Nutrients as described above necessary for the growth of the yeast cells may be added to the fermentation feedstock liquid to allow continuous growth of the yeast cells.

The concentration of the yeast cells in the fermentation culture medium is preferably maintained high within the range which does not cause death of the yeast cells at a high rate due to an environment of the fermentation culture medium which is inappropriate for the growth of the yeast cells, in view of achieving efficient production. For example, by maintaining the concentration of the yeast cells at not less than 5 g/L in terms of dry weight, a good production efficiency can be obtained. As long as an operational trouble of a continuous fermentation device or decrease in the production efficiency is not induced, the upper limit of the concentration of the yeast cells is not restricted.

The operation of continuous culture by allowing the growth of fresh yeast cells having a fermentative production capacity is usually preferably carried out in a single fermentation reaction vessel in view of control of the culture. However, the number of the fermentation reaction vessel(s) is not restricted as long as the continuous culture is carried out to produce the product while allowing the growth of yeast cells. A plurality of fermentation reaction vessels may be used, for example, because of a small volume of each fermentation reaction vessel. In this case, a high productivity of the fermentation product can be obtained even by continuous culture using a plurality of fermentation reaction vessels connected in parallel or in series through pipes.

"Continuation of continuous fermentation" means a state wherein supply of the fermentation feedstock liquid and withdrawal of the culture are carried out continuously or intermittently. Lactic acid is preferably efficiently produced during the period when the continuous fermentation is continued. "Efficient production of lactic acid" means a state wherein the concentration of accumulated lactic acid, the rate of production of lactic acid, and the yield of lactic acid to saccharides are evaluated, and one, preferably two, more preferably all of these is/are high.

"The concentration of accumulated lactic acid" means the concentration of lactic acid contained in the culture, and "a state wherein the concentration of accumulated lactic acid is high" means a state wherein the concentration of accumulated lactic acid is not less than 40 g/L, and the concentration of accumulated lactic acid is preferably 42 g/L, more preferably 44 g/L.

"The rate of production of lactic acid" means the amount of lactic acid produced per unit time, and "a state wherein the rate of production of lactic acid is high" means a state wherein the rate of production of lactic acid represented by Equation 3 is not less than 7.5 g/L/h, preferably not less than 8, more preferably not less than 9 g/L/h:

$P_B$: Rate of production of lactic acid (g/l/h)

$$P_B = V\frac{dP}{dt} = \frac{P(F_M + F_N)}{V} \quad \text{(Equation 3)}$$

$F_M$: Feed rate of culture medium (l/h)
$F_N$: Feed rate of neutralizing agent (l/h)
P: Concentration of product (g/l)
$P_B$: Production rate (g/l/h)
S: Substrate concentration (g/l)
$S_R$: Substrate concentration in culture medium to be supplied (g/l)
t: Time (h)
V: Amount of culture (l)
$Y_{P/S}$: Yield of product (g/g).

"The yield of lactic acid to saccharides" means the ratio of lactic acid produced from a carbon source consumed per unit time, and "a state wherein the yield of lactic acid to saccharides is high" is a state wherein the yield of lactic acid to saccharides represented by Equation 4 is not less than 70%, preferably not less than 75%, more preferably not less than 80%:

$Y_{P/S}$: Yield of product (g/g)

$$Y_{P/S} = V\frac{P}{S_R - S} = \frac{P(F_M + F_N)}{F \times S_R - (F_M + F_N)}. \quad \text{(Equation 4)}$$

The weights of all the saccharides in the culture medium are converted to the mass of glucose.
Example: 1 mol of sucrose is converted to 2 mol of glucose.

Separation and purification of lactic acid contained in the filtered/separated fermentation liquid produced can be carried out by a combination of conventionally-known methods for concentration, distillation, crystallization and the like, and examples of the methods include a method wherein pH of the filtered/separated fermentation liquid is adjusted to not more than 1 followed by extraction with diethyl ether, ethyl acetate or the like, a method wherein lactic acid is allowed to adsorb to an ion-exchange resin followed by washing and elution, a method wherein lactic acid is allowed to react with an alcohol in the presence of an acid catalyst to produce an ester, which is then subjected to distillation, a method wherein lactic acid is crystallized as the calcium salt or the lithium salt, and a separation/purification method wherein the nanofilter disclosed in WO2009/004922 is combined with distillation.

Preferred examples of the continuous fermentation device used in the method for producing lactic acid will now be described referring to the drawings.

FIG. 1 is a schematic side view for explanation of a preferred example of the continuous fermentation device of the membrane separation type used in the method for producing lactic acid by continuous fermentation. FIG. 1 is a representative example of the device in which the separation membrane element is placed outside the fermentation reaction vessel.

In FIG. 1, the continuous fermentation device of the membrane separation type is basically constituted by a fermentation reaction vessel 1, a membrane separation vessel 12 and a pressure difference controlling apparatus 3. In the separation membrane element 2, a porous separation membrane is incorporated. Preferred examples of the porous separation membrane employed include the separation membrane and the separation membrane element disclosed in WO 2002/064240. The membrane separation vessel 12 is connected to a fermentation reaction vessel 1 via a fermentation culture medium circulating pump 11.

In FIG. 1, a culture medium can be fed to the fermentation reaction vessel 1 by a culture medium supplying pump 7, and, as required, the fermentation culture medium in the fermentation reaction vessel 1 can be stirred by a stirrer 5, and further, as required, a necessary gas can be supplied by a gas supplying apparatus 4. The supplied gas can be recovered and recycled, followed by supplying it again with the gas supplying apparatus 4. Further, as required, pH of the fermentation liquid can be adjusted by a pH sensor/controlling apparatus 9 and a pH adjustment solution supplying pump 8, and further, as required, the temperature of the fermentation culture medium can be adjusted by a temperature controller 10, to carry out highly productive fermentative production. The fermentation liquid in the device is circulated between the fermentation reaction vessel 1 and the membrane separation vessel 12 by the fermentation liquid circulating pump 11. The fermentation culture medium containing a fermentation product is filtered and separated by the separation membrane element 2 into the microorganism and the fermentation product, which can be recovered from the device system.

The concentration of the microorganisms in the device system can be maintained high by allowing the microorganisms, which were filtered and separated, to stay in the device system, thereby enabling a highly productive fermentative production. The filtration and separation by the separation membrane element 2 can be carried out by the hydraulic head pressure difference from the fluid level in the membrane separation vessel 12 without using particular power, but, as required, the filtration/separation rate of the separation membrane element 2 and the amount of the fermentation culture medium in the device system can be appropriately controlled by a level sensor 6 and the pressure difference controlling apparatus 3. As required, a necessary gas can be supplied by the gas supplying apparatus 4 into the membrane separation vessel 12. The supplied gas can be recovered and recycled, followed by supplying it again with the gas supplying apparatus 4. The filtration and separation by the separation membrane element 2 can also be carried out, as required, by suction filtration with a pump or the like or by pressurizing the inside of the device system. The polyploid yeast may be cultured in a culture vessel by continuous fermentation and supplied to the fermentation vessel as required. By culturing the polyploid yeast in a culture vessel and supplying it into the fermentation vessel as required, continuous fermentation can be carried out constantly with fresh polyploid yeast highly capable of producing lactic acid, and continuous fermentation can be continued for long time with a high productive performance.

Figure 2:
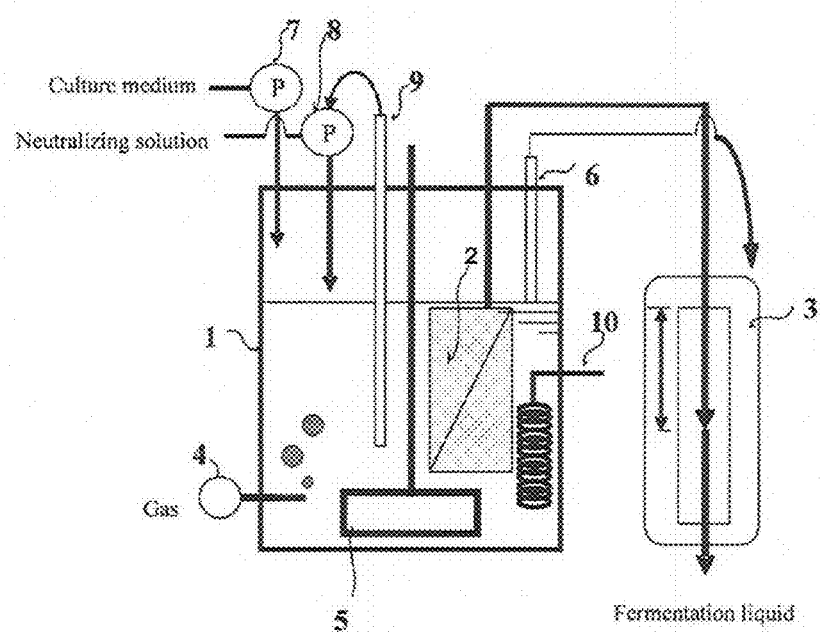
FIG. 2 is a schematic side view for explanation of another continuous fermentation device of the membrane separation type.

FIG. 2 is a schematic side view for explanation of another example of the continuous fermentation device of the membrane separation type. Among the continuous fermentation devices used in the method for producing lactic acid, a representative example in which the separation membrane element is placed inside the fermentation reaction vessel is shown in the schematic view in FIG. 2.

In FIG. 2, the continuous fermentation device of the membrane separation type is basically constituted by a fermentation reaction vessel 1 and a pressure difference controlling apparatus 3. In the separation membrane element 2 in the fermentation reaction vessel 1, a porous membrane is incorporated. Examples of this porous separation membrane which can be employed include the separation membrane and the separation membrane element disclosed in WO 2002/064240. Details of this separation membrane element will be described later.

The example of the continuous fermentation by the continuous fermentation device of the membrane separation type in FIG. 2 will now be explained. By a culture medium supplying pump 7, a culture medium is continuously or intermittently fed to the fermentation reaction vessel 1. The culture medium may be subjected to heat disinfection or heat sterilization, or sterilization treatment using a filter before the feeding, as required. During the fermentative production, as required, the fermentation culture medium in the fermentation reaction vessel 1 is stirred by a stirrer 5 in the fermentation reaction vessel 1. During the fermentative production, as required, a necessary gas may be supplied into the fermentation reaction vessel 1 by a gas supplying apparatus 4. During the fermentative production, as required, pH of the fermentation culture medium in the fermentation reaction vessel 1 may be controlled by a pH sensor/controlling apparatus 9 and a pH adjustment solution supplying pump 8, and as required, the temperature of the fermentation culture medium in the fermentation reaction vessel 1 may be controlled by a temperature controller 10, to carry out highly productive fermentative production. pH and temperature were shown as examples of physicochemical conditions of the fermentation culture medium to be controlled by instrumentation/control apparatuses, but, as required, dissolved oxygen and/or ORP may be controlled, and by an analysis apparatus such as an on-line chemical sensor, the concentration of lactic acid in the fermentation culture medium may be measured followed by controlling physicochemical conditions using as an index the concentration of lactic acid in the fermentation culture medium. When the continuous or intermittent feeding of the culture medium is carried out, the amount of the culture medium to be fed and the rate of feeding thereof are appropriately controlled using as an index the measured value of the physicochemical environment of the fermentation liquid by the instrumentation apparatus.

In FIG. 2, in terms of the fermentation culture medium, the yeast cells and the fermentation product are filtered and separated by a separation membrane element 2 placed in the fermentation reaction vessel 1, and the fermentation product is recovered from the device system. The concentration of the yeast in the device system can be maintained high by allowing the yeast, which was filtered and separated, to stay in the device system, thereby enabling a highly productive fermentative production. The filtration and separation by the separation membrane element 2 can be carried out by the hydraulic head pressure difference from the fluid level in the fermentation reaction vessel 1 without using particular power, but, as required, the filtration/separation rate of the separation membrane element 2 and the amount of the fermentation culture medium in the fermentation reaction vessel 1 can be appropriately controlled by a level sensor 6 and the pressure difference controlling apparatus 3. The filtration/separation by the above-described separation membrane element can also be carried out, as required, by suction filtration with a pump or the like or by pressurizing the inside of the device system. The yeast cells may be cultured in a culture vessel prepared separately and supplied to the fermentation vessel as required. By culturing the yeast cells in a culture vessel and supplying them into the fermentation vessel as required, continuous fermentation can be carried out constantly with fresh yeast cells, and continuous fermentation can be continued for long time with a high productive performance.

The separation membrane element preferably used in the continuous fermentation device used in the method for producing lactic acid will now be described referring to the drawings. In the continuous fermentation device used in the method for producing lactic acid, the separation membrane and the separation membrane element disclosed in WO 2002/064240 may be preferably used.

Figure 3:
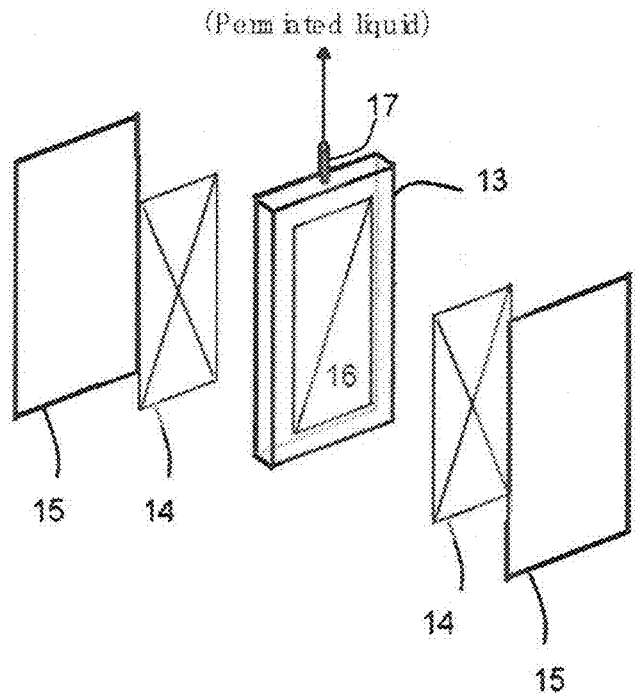
FIG. 3 is a schematic perspective view for explanation of a separation membrane element.

In terms of the example of the separation membrane element, the separation membrane and the separation membrane element disclosed in WO 2002/064240 as preferred examples will now be summarized referring to the drawing. FIG. 3 is a schematic perspective view for explanation of one example of the separation membrane element.

The separation membrane element is constituted, as shown in FIG. 3, of a channel material 14 and the separation membrane 15 arranged in this order on each of the both sides of a supporting plate 13 having rigidity. The supporting plate 13 has a recess 16 on each of the both sides. The fermentation culture medium is filtered through the separation membrane 15. The channel material 14 is used for allowing efficient flow of the permeated liquid, which was filtered through the separation membrane 15, to the supporting plate 13. The permeated liquid allowed to flow to the supporting plate 13 then moves through the recesses 16 on the supporting plate 13, and is recovered to the outside of the continuous fermentation device through a liquid collection pipe 17 which is a means of discharge.

Figure 4:
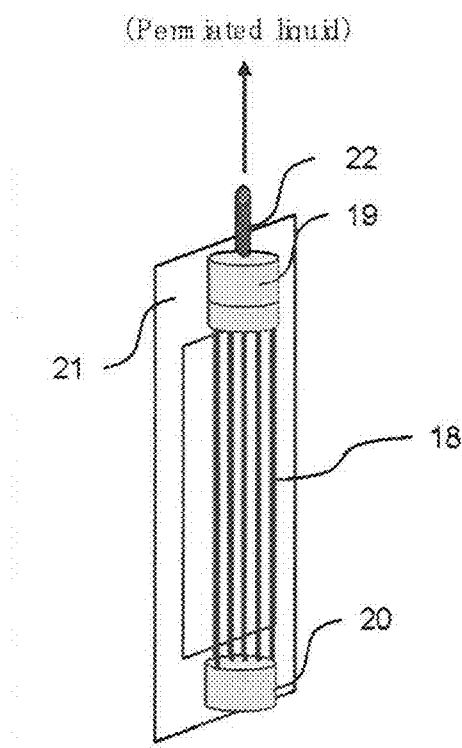
FIG. 4 is a schematic perspective view for explanation of another example of the separation membrane element.

Another example of the separation membrane element shown in FIG. 4 will now be described. FIG. 4 is a cross-sectional view for explaining the other example of the separation membrane element.

In terms of the separation membrane element, as shown in FIG. 4, a separation membrane bundle 18 constituted by hollow fiber membranes is adhered and immobilized in a bundled manner by an upper resin sealing layer 19 and a lower resin sealing layer 20. By the adherence and immobilization by the lower resin sealing layer 20, the hollow portion of the hollow fiber membrane is sealed to provide a structure which prevents leakage of the fermentation culture medium. On the other hand, the upper resin sealing layer 19 does not seal the inner pore of the hollow fiber membrane, to provide a structure which allows the permeated liquid to flow through a liquid collection pipe 22. This separation membrane element may be placed in the continuous fermentation device via a support frame 21. The permeated liquid filtered by the separation membrane bundle 18 flows through the hollow portion of the hollow fiber membrane and is recovered to the outside of the fermentation culture vessel via the liquid collection pipe 22. As the power to recover the permeated liquid, suction filtration by the hydraulic head pressure difference or a pump, liquid, gas or the like, or a method to pressurize the inside of the device system or the like may be used.

Members constituting the separation membrane element of the continuous fermentation device used in the method for producing lactic acid by continuous fermentation are preferably resistant to autoclaving. If the inside of the fermentation device can be sterilized, the risk of contamination with unfavorable fungus bodies can be avoided, and more stable continuous fermentation is possible. The members constituting the separation membrane element are preferably resistant to treatment at a temperature of 121° C. for 15 minutes, which are the conditions of autoclaving. Examples of the members of the separation membrane element which may be preferably selected include metals such as stainless steel and aluminum; and resins such as polyamide resins, fluorocarbon resins, polycarbonate resins, polyacetal resins, polybutylene terephthalate resins, PVDF, modified polyphenylene ether resins and polysulfone resins.

In the continuous fermentation device used in the method for producing lactic acid by continuous fermentation, the separation membrane element may be placed either outside the fermentation vessel or inside the fermentation reaction vessel. In cases where the separation membrane element is placed outside the fermentation reaction vessel, a membrane separation vessel may be separately provided to place the separation membrane element therein, and the fermentation culture medium may be continuously filtered by the separation membrane element while allowing the fermentation culture medium to circulate between the fermentation reaction vessel and the membrane separation vessel.

In the continuous fermentation device used in the method for producing lactic acid by continuous fermentation, the membrane separation vessel is preferably autoclavable. By making the membrane separation vessel autoclavable, contamination can be easily avoided.

EXAMPLES

Our methods will now be described by way of Examples.

Reference Example 1

Preparation of Polyploid Yeast Having Capacity to Produce Lactic Acid

A polyploid yeast having a capacity to produce lactic acid was prepared by polyploidization of yeast having a capacity to produce lactic acid obtained by introduction of the L-lactate dehydrogenase gene derived from Xenopus laevis (hereinafter also referred to as "XLDH") to the *Saccharomyces cerevisiae* NBRC10505 strain. Further, as will be described in detail below, reversion from auxotrophy and/or a temperature-sensitive mutation was/were given to the resulting polyploid yeast. The yeast strains used for preparation of polyploid yeast and the yeast strains prepared by the method described below are shown in FIG. 2. Procedures for the methods of the insertion of the LDH, the giving of the temperature-sensitive mutation and the reversion from auxotrophy will be described in detail below.

(Part 1)
Construction of Vector for Expression of L-LDH (XLDH) Derived from *Xenopus laevis*

Cloning of XLDH (SEQ ID NO:1) was carried out by PCR. For the PCR, a phagemid DNA prepared from a cDNA library (manufactured by STRATAGENE) derived from kidney of *Xenopus laevis* according to the manufacturer's protocol was used as the template.

For the PCR amplification reaction, KOD-Plus polymerase (manufactured by Toyobo Co., Ltd.) was used, and the reaction buffer, the dNTP mix and the like included therein were used. The phagemid DNA prepared according to the manufacturer's protocol as described above was used to prepare 50 μl of a reaction system containing 50 ng/sample of the phagemid DNA, 50 pmol/sample of primers and 1 U/sample of KOD-Plus polymerase. The reaction solution was subjected to denaturation by a PCR amplification device iCycler (manufactured by BIO-RAD) at a temperature of 94° C. for 5 minutes, and this was followed by 30 cycles of: 94° C. (heat denaturation) for 30 seconds, 55° C. (annealing of the primers) for 30 seconds and 68° C. (extension of the complementary strand) for 1 minute. Thereafter, the reaction solution was cooled to a temperature of 4° C. The primers (SEQ ID NOs:2 and 3) for amplification of the gene were prepared such that the SalI-recognition sequence and the NotI recognition sequence were added to the 5'-end and the 3'-end, respectively.

The PCR amplification fragment was purified and phosphorylated by T4 polynucleotide Kinase (manufactured by TAKARA BIO INC.) at its ends, and ligated to the pUC118 vector (which had been preliminarily digested with a restriction enzyme HincII and the digested ends had been subjected to dephosphorylation treatment). The ligation was carried out using DNA Ligation Kit Ver.2 (manufactured by TAKARA BIO INC.). Competent cells of *E. coli* DH5α (manufactured by TAKARA BIO INC.) were transformed with the ligation solution and plated on an LB plate containing 50 μg/mL of an antibiotic ampicillin, followed by culturing overnight. Plasmid DNAs were collected from grown colonies by miniprep and digested with restriction enzymes SalI and NotI, followed by selection of a plasmid to which the LDH gene derived from *Xenopus laevis* was inserted. This series of operation was entirely carried out according to the manufacturer's protocol.

Figure 5:
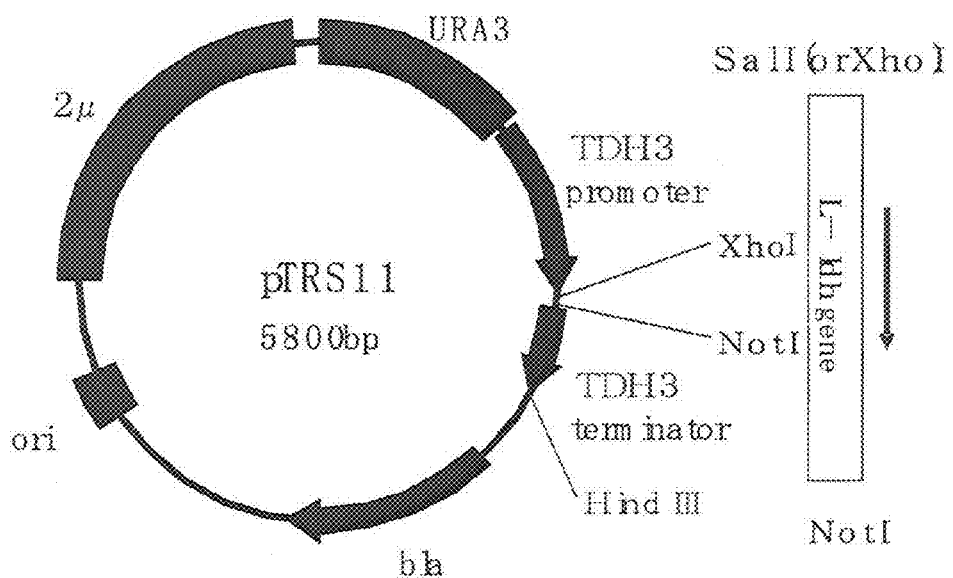
FIG. 5 is a vector for expression of a lactate dehydrogenase gene.

The pUC118 vector to which XLDH was inserted was digested with restriction enzymes SalI and NotI, and the DNA fragments were separated by 1% agarose gel electrophoresis, followed by purification of the fragment containing XLDH according to a conventional method. The obtained fragment was ligated to the XhoI/NotI-digestion site in the expression vector pTRS11 shown in FIG. 5, and plasmid DNA was collected by the same method as described above, followed by digestion thereof with restriction enzymes XhoI and NotI and selection of pTRS102 which is an expression vector to which XLDH was inserted.

The method for inserting LDH to the PDC1, SED1 and TDH3 loci using the thus obtained pTRS102 as the template for XLDH will now be described.

(Part 2)
Insertion of LDH to Yeast Chromosome PDC1 Locus

Using pTRS102 as the template for amplification and oligonucleotides (SEQ ID NOs:4 and 5) as the primer set, PCR was carried out to amplify a PCR fragment of 1.3 kb comprising XLDH and the TDH3 terminator sequence. SEQ ID NO:4 was designed such that the sequence corresponding to the region of 60 by in the immediate upstream of the initiation codon of the PDC1 gene was added.

Subsequently, using the plasmid pTRS424 as the template for amplification and oligonucleotides (SEQ ID NOs:6 and 7) as the primer set, PCR was carried out to amplify a PCR fragment of 1.2 kb comprising the TRP1 gene which is the selection marker for the yeast. SEQ ID NO:7 was designed such that the sequence corresponding to the region of 60 by in the immediate downstream of the termination codon of the PDC1 gene was added.

Each DNA fragment was separated by 1% agarose gel electrophoresis and purified according to a conventional method. Using a mixture of the obtained 1.3 kb fragment and 1.2 kb fragment as the template for amplification and oligonucleotides (SEQ ID NOs:4 and 7) as the primer set, PCR was carried out to amplify a PCR fragment of about 2.5 kb in which XLDH, the TDH3 terminator and the TRP1 gene were linked and the sequences corresponding to the region of 60 by in the immediate upstream and the region of 60 by in the immediate downstream of the PDC1 gene were added to the 5'-end and the 3'-end, respectively.

The PCR fragment was separated by 1% agarose gel electrophoresis and purified according to a conventional method, followed by transformation and culturing on a culture medium to which tryptophan was not supplemented. By this, a transformant having XLDH introduced to the downstream of the PDC1 gene promoter on the chromosome was selected.

To confirm that the thus obtained transformant was yeast having the *Xenopus laevis*-derived L-LDH introduced to the downstream of the PDC1 gene promoter on the chromosome, the following operations were carried out. First, the genomic DNA of the transformant was prepared with a genomic DNA extraction kit Dr. GenTLE (manufactured by TAKARA BIO INC.), and using the resulting genomic DNA as the template for amplification and oligonucleotides (SEQ ID NOs:7 and 8) as the primer set, PCR was carried out to confirm that a DNA fragment of about 2.8 kb was amplified. An untransformed strain yields a DNA fragment of about 2.1 kb by amplification by the above PCR.

(Part 3)
Insertion of LDH to Yeast Chromosome SED1 Locus

In terms of the introduction into the SED1 locus, using pTRS102 prepared in Reference Example 1 as the template for amplification and oligonucleotides (SEQ ID NOs:5 and 9) as the primer set, PCR was carried out to amplify a PCR fragment of 1.3 kb comprising the LDH gene derived from *Xenopus laevis* and the TDH3 terminator sequence. SEQ ID NO:9 was designed such that the sequence corresponding to the region of 60 by in the immediate upstream of the initiation codon of the SED 1 gene was added.

Subsequently, using the plasmid pRS423 as the template for amplification and oligonucleotides (SEQ ID NOs:6 and 10) as the primer set, PCR was carried out to amplify a PCR fragment of about 1.3 kb comprising the HIS3 gene which is the selection marker for the yeast. SEQ ID NO:10 was designed such that the sequence corresponding to the region of 60 by in the immediate downstream of the termination codon of the SED1 gene was added.

Each DNA fragment was separated by 1% agarose gel electrophoresis and purified according to a conventional method. Using a mixture of the obtained two kinds of fragments having lengths of about 1.3 kb as the template for amplification and oligonucleotides (SEQ ID NOs:9 and 10) as the primer set, PCR was carried out to amplify a PCR fragment of about 2.6 kb in which the LDH derived from *Xenopus laevis*, the TDH3 terminator and the HIS3 gene were linked and the sequences corresponding to the regions of 60 by in the immediate upstream and downstream of the SED1 gene were added to the 5'-end and the 3'-end, respectively.

The PCR fragment was separated by 1% agarose gel electrophoresis and purified according to a conventional method, followed by transformation and culturing on a culture medium to which histidine was not supplemented. By this, a transformant having XLDH introduced to the downstream of the SED1 gene promoter on the chromosome was selected.

To confirm that the thus obtained transformant was a yeast having XLDH introduced to the downstream of the SED1 gene promoter on the chromosome, the following operations were carried out. First, the genomic DNA of the transformant was prepared with a genomic DNA extraction kit Dr. GenTLE (manufactured by TAKARA BIO INC.), and using the resulting genomic DNA as the template for amplification and oligonucleotides (SEQ ID NOs:11 and 12) as the primer set, PCR was carried out to confirm that a DNA fragment of about 2.9 kb was amplified. An untransformed strain yields a DNA fragment of about 1.4 kb by amplification by the above PCR.

(Part 4)
Insertion of LDH to Yeast Chromosome TDH3 Locus

In terms of the introduction into the TDH3 locus, a plasmid in which the TDH3 terminator of pTRS102 was replaced with the ADH1 terminator was prepared.

First, the genomic DNA was prepared from the NBRC10505 strain with a genomic DNA extraction kit "Dr. GenTLE" (manufactured by TAKARA BIO INC.), and using the extracted genomic DNA as the template and oligonucleotides (SEQ ID NOs:13 and 14) as the primer set, PCR was carried out to amplify a PCR fragment containing the ADH1 promoter. SEQ ID NO:13 was designed such that the NotI recognition sequence was added to its 5'-end and SEQ ID NO:14 was designed such that the HindIII recognition sequence was added to its 3'-end.

The PCR amplification fragment was purified and phosphorylated by T4 polynucleotide Kinase (manufactured by TAKARA BIO INC.) at its ends, and ligated to the pUC118 vector (which had been preliminarily digested with a restriction enzyme HincII and the digested ends had been subjected to dephosphorylation treatment). Competent cells of E. coli DH5α (manufactured by TAKARA BIO INC.) were transformed with the ligation solution and plated on an LB plate containing 50 μg/mL of an antibiotic ampicillin, followed by culturing overnight. From grown colonies, plasmid DNAs were collected by miniprep and digested with restriction enzymes NotI and HindIII, followed by selection of a plasmid to which the ADH1 terminator was inserted. The prepared plasmid will be referred to as pUC118-ADH1t.

Subsequently, pUC118-ADH1t was digested with restriction enzymes NotI and HindIII, and the DNA fragments were separated by 1% agarose gel electrophoresis, followed by purification of the fragment containing the ADH1 terminator according to a conventional method. The obtained fragment containing the ADH1 terminator was ligated to the NotI/HindIII-digestion site in pTRS102 and plasmid DNAs were collected by the same method as described above, followed by digestion thereof with restriction enzymes NotI and HindIII and selection of a plasmid in which the TDH3 terminator was replaced with the ADH1 terminator. The thus prepared plasmid will be hereinafter referred to as pTRS150.

Using this pTRS150 as the template and oligonucleotides (SEQ ID NOs:15 and 16) as the primer set, PCR was carried out to amplify a PCR fragment of 1.3 kb comprising the frog-derived L-LDH gene and the ADH1 terminator sequence. The primer having the sequence of SEQ ID NO:16 was designed such that the sequence corresponding to the region of 60 by in the immediate upstream of the initiation codon of the TDH3 gene was added.

Subsequently, using the plasmid pRS426 as the template for amplification and oligonucleotides (SEQ ID NOs:17 and 18) as the primer set, PCR was carried out to amplify a PCR fragment of 1.2 kb comprising the URA3 gene which is the selection marker for the yeast. The primer having the sequence of SEQ ID NO:18 was designed such that the sequence corresponding to the region of 60 by in the immediate downstream of the termination codon of the TDH3 gene was added.

Each DNA fragment was separated by 1% agarose gel electrophoresis and purified according to a conventional method. Using a mixture of the obtained 1.3 kb fragment and 1.2 kb fragment as the template for amplification and oligonucleotides (SEQ ID NOs:16 and 18) as the primer set, PCR was carried out to amplify a PCR fragment of about 2.5 kb in which XLDH, the ADH1 terminator and the URA3 gene were linked.

The PCR fragment was separated by 1% agarose gel electrophoresis and purified according to a conventional method, followed by transformation and culturing on a culture medium to which uracil was not supplemented. By this, a transformant having XLDH introduced to the downstream of the TDH3 gene promoter on the chromosome was selected.

To confirm that the thus obtained transformant was yeast having XLDH introduced to the downstream of the TDH3 gene promoter on the chromosome, the following operations were carried out. First, the genomic DNA of the transformant was prepared with a genomic DNA extraction kit "Dr. GenTLE" (manufactured by TAKARA BIO INC.), and using the resulting genomic DNA as the template for amplification and oligonucleotides (SEQ ID NOs:19 and 20) as the primer set, PCR was carried out to confirm that a DNA fragment of about 2.8 kb was amplified. An untransformed strain yields a DNA fragment of about 2.1 kb by amplification by the above PCR.

(Part 5)
Obtaining Yeast Having PDC5 Gene Having Temperature-Sensitive Mutation

A temperature-sensitive mutation was given by mating the yeast SW015 strain having a temperature-sensitive mutation in the pdc5 gene described in JP 2008-048726 A with the yeast to which a temperature-sensitive mutation was to be given. In this diploid yeast, ascus formation was allowed to occur in an ascus formation medium, and the resulting asci were anatomized with a micromanipulator to obtain respective haploid cells. Auxotrophy was analyzed for each of the haploid cells to select a strain having XLDH inserted into one of the PDC1 gene, SED1 gene and TDH1 locus and further having a temperature-sensitive mutation in the PDC5 gene (incapable of growing at 34° C.).

The method of reversion from auxotrophy will now be described.

(Part 6)
Preparation of Strain Showing Reversion from Lysine Auxotrophy

In cases of reversion from lysine auxotrophy, the following method was used. Using the genomic DNA of BY4741 manufactured by Funakoshi as the template and oligonucleotides (SEQ ID NOs:21 and 22) as the primer set, PCR was carried out to amplify a PCR fragment of about 2 kb corresponding to the former half of the LYS2 gene. The PCR fragment was separated by 1% agarose gel electrophoresis and purified according to a conventional method, followed by transformation to cancel the amber mutation of the LYS2 gene. By culturing the yeast on a culture medium to which lysine was not supplemented, a transformant showing reversion of lysine synthesis capacity was selected.

To confirm that the thus obtained transformant was yeast whose amber mutation of the LYS2 gene was canceled, the following operations were carried out. First, diploid cells were obtained by mating the obtained transformant with the 20GY77 strain having the wild type LYS2 gene. In the diploid cells, ascus formation was allowed to occur in an ascus formation medium. The resulting asci were anatomized with a micromanipulator to obtain respective haploid cells, and auxotrophy was analyzed for each of the haploid cells. All the obtained haploid cells were confirmed to have the lysine synthesis capacity. In cases where reversion of the lysine synthesis capacity occurred without canceling the mutation of the LYS2 gene, cells having no lysine synthesis capacity are obtained among the haploid cells obtained as above.

(Part 7)
Obtaining Strain Showing Reversion from Leucine Auxotrophy

In the case of reversion from leucine auxotrophy, the following method was used. Using the plasmid PRS425 as the template and oligonucleotides (SEQ ID NOs:23 and 24) as the primer set, PCR was carried out to amplify a PCR fragment of about 2 kb of the LEU2 gene. The PCR fragment was separated by 1% agarose gel electrophoresis and purified according to a conventional method, followed by transformation to cancel the mutation of the LEU2 gene. By culturing the yeast on a culture medium to which leucine was not supplemented, a transformant showing reversion of the leucine synthesis capacity was selected.

To confirm that the thus obtained transformant was yeast whose mutation of the LEU2 gene was canceled, the following operations were carried out. First, diploid cells were obtained by mating the obtained transformant with the *Saccharomyces cerevisiae* 20GY7 strain having the wild type LEU2 gene. In the diploid cells, ascus formation was allowed to occur in an ascus formation medium. The resulting asci were anatomized with a micromanipulator to obtain respective haploid cells, and auxotrophy was analyzed for each of the haploid cells. All the obtained haploid cells were confirmed to have the leucine synthesis capacity. In cases where reversion of the leucine synthesis capacity occurred without canceling the mutation of the LEU2 gene, cells having no leucine synthesis capacity are obtained among the haploid cells obtained as above.

(Part 8)
Obtaining Strain Showing Reversion from Adenine Auxotrophy

In the case of reversion from adenine auxotrophy, the following method was used. Using the plasmid PRS422 as the template and oligonucleotides (SEQ ID NOs:25 and 26) as the primer set, PCR was carried out to amplify a PCR fragment of about 2 kb of the ADE2 gene. The PCR fragment was separated by 1% agarose gel electrophoresis and purified according to a conventional method, followed by transformation to cancel the mutation of the ADE2 gene. By culturing the yeast on a culture medium to which adenine was not supplemented, a transformant showing reversion of the adenine synthesis capacity was selected.

To confirm that the thus obtained transformant was yeast whose mutation of the AED2 gene was canceled, the following operations were carried out. First, diploid cells were obtained by mating the obtained transformant with the *Saccharomyces cerevisiae* 20GY7 strain having the wild type ADE2 gene. In the diploid cells, ascus formation was allowed to occur in an ascus formation medium. The resulting asci were anatomized with a micromanipulator to obtain respective haploid cells, and auxotrophy was analyzed for each of the haploid cells. All the obtained haploid cells were confirmed to have the adenine synthesis capacity. In cases where reversion of the adenine synthesis capacity occurred without canceling the mutation of the ADE2 gene, cells having no adenine synthesis capacity are obtained among the haploid cells obtained as above.

(Part 9)
Obtaining Strain Showing Reversion from Uracil Auxotrophy

In the case of reversion from uracil auxotrophy, the following method was used. Using the plasmid pRS426 as the template and oligonucleotides (SEQ ID NOs:27 and 28) as the primer set, PCR was carried out to amplify a PCR fragment of about 2 kb of the URA3 gene. The PCR fragment was separated by 1% agarose gel electrophoresis and purified according to a conventional method, followed by transformation to cancel the mutation of the URA3 gene. By culturing the yeast on a culture medium to which uracil was not supplemented, a transformant showing reversion of the uracil synthesis capacity was selected.

To confirm that the thus obtained transformant was yeast whose mutation of the URA3 gene was canceled, the following operations were carried out. First, diploid cells were obtained by mating the obtained transformant with the *Saccharomyces cerevisiae* 20GY7 strain having the wild type URA3 gene. In the diploid cells, ascus formation was allowed to occur in an ascus formation medium. The resulting asci were anatomized with a micromanipulator to obtain respective haploid cells, and auxotrophy was analyzed for each of the haploid cells. All the obtained haploid cells were confirmed to have the uracil synthesis capacity. In cases where reversion of the uracil synthesis capacity occurred without canceling the mutation of the URA3 gene, cells having no uracil synthesis capacity are obtained among the haploid cells obtained as above.

(Part 10)
Obtaining Polyploid Strain Having Capacity to Produce Lactic Acid

By mating the transformants obtained by the combination of the methods of Parts 1 to 9, a diploid prototrophic strain having no auxotrophy was obtained. In the diploid prototrophic strain, ascus formation was allowed to occur in an ascus formation medium, and the resulting asci were anatomized with a micromanipulator to obtain respective haploid cells. Auxotrophy was analyzed for each of the haploid cells, and strains grown in SD medium (Table 1) were judged as having reversion from auxotrophy and regarded as haploid prototrophic strains.

TABLE 2

| Strain name | Mating type | Genotype |
| --- | --- | --- |
| H1003 | MATa/α | Δpdc1::XLDH-TRP1 Δsed1::XLDH-HIS3 Δtdh3::XLDH-URA3 pdc5$^{ts-9}$ Polyploid yeast (prototrophic) |
| SU014 | MATa/α | Δpdc1::XLDH-TRP1 Δsed1::XLDH-URA3 Δtdh3::XLDH-HIS3 pdc5$^{ts-9}$ lys2-801 leu2-Δ Polyploid yeast (auxotrophic) |
| SE001 | MATa/α | Δpdc1::XLDH-TRP1 Δtdh3::XLDH-URA3 pdc5$^{ts-9}$ Polyploid yeast (prototrophic) |
| H1003-1B | MATa | Δpdc1::XLDH-TRP1 Δsed1::XLDH-HIS3 Δtdh3::XLDH-URA3 pdc5$^{ts-9}$ Haploid yeast (prototrophic) |
| SU014-3B | MATa | Δpdc1::XLDH-TRP1 Δsed1::XLDH-URA3 Δtdh3::XLDH-HIS3 pdc5$^{ts-9}$ lys2-801 leu2-Δ1 Haploid yeast (auxotrophic) |
| SE001-1A | MATa | Δpdc1::XLDH-TRP1 Δtdh3::XLDH-HIS3 pdc5$^{ts-9}$ lys2-801 leu2-Δ1 Haploid yeast (prototrophic) |
| SW015 | MATα | ura3-52 trp1-Δ63 his3-Δ200 pdc5ts-9 lys2-801 leu2-Δ1 Haploid yeast (auxotrophic) | pdc5$^{ts-9}$: Temperature-sensitive mutation

Reference Example 2

Method for Quantifying Lactic Acid

Lactic acid was confirmed by measuring the amount of lactic acid in the centrifugation supernatant of the culture by HPLC under the following conditions;

Column: Shim-Pack SPR-H (manufactured by Shimadzu Corporation)
Mobile phase: 5 mM p-toluenesulfonic acid (flow rate: 0.8 mL/min.)
Reaction solution: 5 mM p-toluenesulfonic acid, 20 mM Bis-Tris, 0.1 mM EDTA·2Na (flow rate: 0.8 mL/min.)
Detection method: electric conductivity
Temperature: 45° C.

Measurement of the optical purity of L-lactic acid was carried out by HPLC under the following conditions:
Column: TSK-gel Enantio L1 (manufactured by produced by Tosoh Corporation)
Mobile phase: 1 mM aqueous copper sulfate solution
Flow rate: 1.0 ml/min.
Detection method: UV 254 nm
Temperature: 30° C.

The optical purity of L-lactic acid was calculated by the following equation:

$$\text{Optical purity (\%)}=100\times(L-D)/(L+D)$$

(wherein L represents the concentration of L-lactic acid, and D represents the concentration of D-lactic acid).

Reference Example 3

Preparation of Porous Membrane (Part 1)

A polyvinylidene fluoride (PVDF) resin and N,N-dimethylacetamide (DMAc) were used as a resin and a solvent, respectively, and these were sufficiently stirred at a temperature of 90° C. to obtain a starting solution having the following composition:
[Starting Solution]
  PVDF: 13.0% by weight
  DMAc: 87.0% by weight.

Subsequently, the above starting solution was cooled to a temperature of 25° C. and applied to a polyester fiber nonwoven fabric (porous base material) having a density of 0.48 g/cm$^3$ and a thickness of 220 μm which had been preliminarily attached on a glass plate, and the resultant was immediately immersed in a coagulation bath at a temperature of 25° C. having the following composition for 5 minutes to obtain a flat membrane having a porous resin layer formed on the porous base material:
[Coagulation Bath]
  Water: 30.0% by weight
  DMAc: 70.0% by weight.

This porous membrane was peeled from the glass plate and immersed three times in hot water at a temperature of 80° C. to wash out DMAc, to obtain a separation membrane. By observation of an area of 9.2 μm×10.4 μm on the surface of the porous resin layer with a scanning electron microscope at a magnification of 10,000×, it was revealed that the average diameter of all the observable pores was 0.1 μm. Subsequently, the above separation membrane was evaluated for its pure water permeability coefficient, and it was turned out to be $50\times10^{-9}$ m$^3$/m$^2$/s/Pa. The standard deviation of the average pore size was 0.035 μm, and the membrane surface roughness was 0.06 μm.

Reference Example 4

Preparation of Porous Membrane (Part 2)

A vinylidene fluoride homopolymer having a weight average molecular weight of 417,000 and γ-butyrolactone were dissolved at a temperature of 170° C. at ratios of 38% by weight and 62% by weight, respectively, to prepare a starting solution. This starting solution was extruded from a mouthpiece while being accompanied by γ-butyrolactone as a fluid for formation of the hollow portion, followed by cooling and solidifying the resultant in a cooling bath at 20° C. comprising aqueous 80% by weight γ-butyrolactone solution, to prepare a hollow fiber membrane.

Subsequently, 14% by weight of a vinylidene fluoride homopolymer having a weight average molecular weight of 284,000, 1% by weight of cellulose acetate propionate (manufactured by Eastman Chemical Company, CAP482-0.5), 77% by weight of N-methyl-2-pyrrolidone, 5% by weight of polyoxyethylene coconut oil fatty acid sorbitan (manufactured by Sanyo Chemical Industries, Ltd.; trade name "IONET T-20C" (registered trademark)) and 3% by weight of water were mixed and dissolved at a temperature of 95° C., to adjust a starting solution. This starting solution was evenly applied to the surface of the hollow fiber membrane and immediately allowed to coagulate in a water bath, to prepare the hollow fiber membrane (porous membrane). The average pore size of the surface in the side of the liquid to be processed of the obtained hollow fiber membrane (separation membrane) was 0.05 μm. The pure water permeability coefficient of the hollow fiber membrane which is the above separation membrane was evaluated to be $5.5\times10^{-9}$ m$^3$/m$^2$·s·Pa. The standard deviation of the average pore size was 0.006 μm.

Example 1

Production of Lactic Acid by Continuous Fermentation Using Polyploid (Prototrophic) Yeast Having Capacity to Produce Lactic Acid (Part 1)

Using the yeast HI003 strain prepared in Reference Example 1, lactic acid was produced with the continuous fermentation device of FIG. 1 and the SC4 medium having the composition shown in Table 3. The culture medium was autoclaved at 121° C. for 15 minutes before use. As the members for the separation membrane element, stainless steel and polysulfone resin molded products were used. As the separation membrane, the porous membrane prepared in the above-described Reference Example 3 was used.

TABLE 3

| | |
|---|---|
| YEAST NITROGEN W/O AA & AS (manufactured by Difco) | 1.7 g |
| Yeast Synthetic Drop-out Medium Supplements without tryptophan (manufactured by SIGMA) | 3.84 g |
| Ammonium sulfate | 1.5 g |
| Glucose | 100 g |
| | up to 1 L |

The operation conditions in Example 1 were as follows:
Fermentation reaction vessel capacity: 2 (L)
Membrane separation vessel capacity: 0.5 (L)
Separation membrane used: polyvinylidene fluoride filter (Reference Example 3)
Effective filtration area of the membrane separation element: 60 cm$^2$
Temperature adjustment: 32 (° C.)
Ventilation volume in the fermentation reaction vessel: 0.05 (L/min.)
Ventilation volume in the membrane separation vessel: 0.3 (L/min.)
Stirring rate in the fermentation reaction vessel: 100 (rpm)
pH adjustment: adjusted to pH 5 with 8 N Ca(OH)$_2$
Feed rate of lactic acid fermentation medium: variably controlled within the range of 50 to 300 ml/hr.

Amount of the liquid circulated by the fermentation liquid circulating device: 0.1 (L/min.)

Control of the amount of permeation of the liquid through the membrane: control of the flow rate by the transmembrane pressure difference (controlled at a transmembrane pressure difference of 0.1 kPa to less than 20 kPa).

The culture vessel comprising the separation membrane element was autoclaved at 121° C. for 20 minutes.

For evaluation of the concentration of lactic acid which is the product, the above-described HPLC shown in Reference Example 2 was used, and for measurement of the glucose concentration, "Glucose Test Wako C" (registered trademark) (manufactured by Wako Pure Chemical Industries, Ltd.) was used.

First, the HI003 strain was cultured in 5 ml of SC4 medium in a test tube overnight with shaking to obtain a culture (pre-pre-preculture). The obtained culture was inoculated in 100 ml of fresh SC4 medium and subjected to culture in a 500 ml Sakaguchi flask for 24 hours at a temperature of 30° C. with shaking (pre-preculture). The pre-preculture was inoculated in 1.5 L of SC4 medium in the continuous fermentation device shown in FIG. 1, and the fermentation reaction vessel 1 was stirred with the stirrer 5 attached thereto. The ventilation volume, temperature and pH in the fermentation reaction vessel 1 were adjusted and culture was carried out for 24 hours without operating the fermentation culture medium circulating pump 11 (preculture). Immediately after the completion of the preculture, the fermentation culture medium circulating pump 11 was operated, and production of lactic acid by continuous fermentation was carried out by continuous culture under the conditions of, in addition to the operating conditions under which the preculture was carried out, aeration of the membrane separation vessel 12, continuous supply of SC4 medium and control of the amount of permeation of the liquid through the membrane such that the amount of the fermentation culture medium in the continuous fermentation device of the membrane separation type became 2 L. The amount of permeation of the liquid through the membrane during the continuous fermentation test was appropriately controlled by the pressure difference controlling apparatus 3 such that transmembrane pressure difference became not less than 0.1 kPa and less than 20 kPa. The concentration of the produced lactic acid and the concentration of the remaining glucose in the fermentation culture medium permeated through the membrane were measured as appropriate.

As a result of 800 hours of the continuous fermentation test, stable production of lactic acid by continuous fermentation was possible as shown in Table 6.

Example 2

Production of Lactic Acid by Continuous Fermentation Using Polyploid (Prototrophic) Yeast Having Capacity to Produce Lactic Acid (Part 2)

Using the yeast HI003 strain prepared in Reference Example 1, lactic acid was produced with the continuous fermentation device shown in FIG. 2 and the SC4 medium having the composition shown in Table 3. The culture medium was autoclaved at 121° C. for 15 minutes before use. As the members for the separation membrane element, stainless steel and poly-sulfone resin molded products were used. As the separation membrane, the porous separation membrane prepared in the above-described Reference Example 3 was used.

The operation conditions in Example 2 were as follows:
Fermentation reaction vessel capacity: 2 (L)
Separation membrane used: polyvinylidene fluoride filter (Reference Example 3)
Effective filtration area of the membrane separation element: 120 cm$^2$
Temperature adjustment: 32 (° C.)
Ventilation volume in the fermentation reaction vessel: 0.05 (L/min.)
Feed rate of the lactic acid fermentation medium: variably controlled within the range of 50 to 300 ml/hr.
Stirring rate in the fermentation reaction vessel: 800 (rpm)
pH adjustment: adjusted to pH 5 with 8 N Ca(OH)$_2$
Control of the amount of permeation of the liquid through the membrane: control of the flow rate by the transmembrane pressure difference (controlled at a transmembrane pressure difference of 0.1 kPa to less than 20 kPa).

The culture vessel comprising the separation membrane element was autoclaved at 121° C. for 20 minutes.

For evaluation of the concentration of lactic acid which is the product, the above-described HPLC shown in Reference Example 2 was used, and for measurement of the glucose concentration, "Glucose Test Wako C" (registered trademark) (manufactured by Wako Pure Chemical Industries, Ltd.) was used.

First, the HI003 strain was cultured in 5 ml of SC4 medium in a test tube overnight with shaking to obtain a culture (pre-pre-preculture). The obtained culture was inoculated in 100 ml of fresh SC4 medium and subjected to culture in a 500 ml Sakaguchi flask for 24 hours at a temperature of 30° C. with shaking (pre-preculture). The pre-preculture was inoculated to 1.5 L of SC4 medium in the continuous fermentation device of the membrane separation type shown in FIG. 2, and the fermentation reaction vessel 1 was stirred with the stirrer 5 attached thereto at 400 rpm. The ventilation volume, temperature and pH in the fermentation reaction vessel 1 were adjusted and culture was carried out for 24 hours (preculture). Immediately after the completion of the preculture, production of lactic acid by continuous fermentation was carried out by continuous supply of SC4 medium and continuous culture while controlling the amount of permeation of the liquid through the membrane such that the amount of the fermentation culture medium in the continuous fermentation device of the membrane separation type became 1.5 L. The amount of permeation of the liquid through the membrane during the continuous fermentation test was appropriately controlled by the pressure difference controlling apparatus 3 such that the transmembrane pressure difference became not less than 0.1 kPa and less than 20 kPa. The concentration of the produced lactic acid and the concentration of the remaining glucose in the fermentation culture medium permeated through the membrane were measured as appropriate. Further, the yield of lactic acid to saccharides and the rate of production of lactic acid, which were calculated from the fed glucose calculated from the concentrations of lactic acid and glucose, were measured.

The result of 800 hours of the continuous fermentation test is shown in Table 6. Stable production of lactic acid by continuous fermentation was possible by the method for production of lactic acid using the continuous fermentation device shown in FIG. 2.

Example 3

Production of Lactic Acid by Continuous Fermentation Using Polyploid (Prototrophic) Yeast Having Capacity to Produce Lactic Acid (Part 3)

The operations and evaluations were carried out under the same conditions as in Example 1 except that the porous membrane prepared in the above-described Reference Example 4 was used as the separation membrane. The result of 750 hours of the continuous fermentation test is shown in Table 6. Stable production of lactic acid by continuous fermentation was possible by our method for production of lactic acid.

Example 4

Production of Lactic Acid by Continuous Fermentation Using Polyploid (Prototrophic) Yeast Having Capacity to Produce Lactic Acid (Part 4)

The operations and evaluations were carried out under the same conditions as in Example 2 except that the porous separation membrane prepared in the above-described Reference Example 4 was used as the separation membrane. The result of 770 hours of a fermentation test is shown in Table 6. Stable production of lactic acid by continuous fermentation was possible by our method for production of lactic acid.

Comparative Example 1

Production of Lactic Acid by Batch Fermentation Using Polyploid (Prototrophic) Yeast Having Capacity to Produce Lactic Acid Batch fermentation, which is the most typical mode of fermentation using yeast cells, was carried out to evaluate its L-lactic acid productivity. Using the SC4 medium shown in Table 3, batch fermentation test was carried out using only the fermentation reaction vessel 1 in the continuous fermentation device of the membrane separation type in FIG. 1. The culture medium was autoclaved at 121° C. for 15 minutes before use. Also in this Comparative Example 1, the yeast HI003 strain prepared in the above-described Reference Example 1 was used as the yeast, and the concentration of lactic acid, which is the product, and saccharides in the culture were quantified using the HPLC shown in the above-described Reference Example 2.

The operation conditions in Comparative Example 1 were as follows:

Fermentation reaction vessel capacity: 2 (L)

Temperature adjustment: 30 (° C.)

Ventilation volume in the fermentation reaction vessel: 0.05 (L/min.)

Stirring rate in the fermentation reaction vessel: 100 (rpm)

pH adjustment: adjusted to pH 5 with 8 N $Ca(OH)_2$.

The culture vessel was autoclaved at 121° C. for 20 minutes.

First, the HI003 strain was cultured in 5 ml of a lactic acid fermentation medium in a test tube overnight with shaking (pre-preculture). The pre-preculture was inoculated in 100 ml of a fresh lactic acid fermentation medium and subjected to culture in a 500 ml Sakaguchi flask for 24 hours with shaking (preculture). The preculture was inoculated in 1 L of the lactic acid fermentation medium in the continuous fermentation device of the membrane separation type, and the fermentation reaction vessel 1 was stirred with the stirrer 5 attached thereto at 100 rpm for aeration of the fermentation reaction vessel 1. The temperature and pH were adjusted and batch fermentation culture was carried out without operating the fermentation culture medium circulating pump 11. The amount of growth of the yeast at this time was 14 in terms of absorbance at 600 nm. The result of the batch fermentation is shown in Table 6. The fermentation time was short, and the yield of lactic acid to saccharides and the rate of production of lactic acid were inferior to those in Examples.

Comparative Example 2

Production of Lactic Acid by Continuous Fermentation Using Haploid Yeast (Prototrophic) (Part 1)

The evaluations were carried out under the same conditions as in Example 1 except that the yeast HI003-1B strain prepared in Reference Example 1 was used. As a result, the transmembrane pressure difference became not less than 20 kPa 600 hours later and the culture was terminated. The result of the continuous fermentation test is shown in Table 6. As a result, it was revealed that lactic acid can be produced longer and more stably when polyploid yeast is used.

Comparative Example 3

Production of Lactic Acid by Continuous Fermentation Using Haploid Yeast (Prototrophic) (Part 2)

The operations and evaluations were carried out under the same conditions as in

Example 2 except that the yeast HI003-1B strain prepared in Reference Example 1 was used. As a result, the transmembrane pressure difference became not less than 20 kPa at 600 hours and the culture was terminated. The result of the continuous fermentation test is shown in Table 6. As a result, it was revealed that lactic acid can be produced longer and more stably when polyploid yeast is used.

Comparative Example 4

Production of Lactic Acid by Continuous Fermentation Using Haploid Yeast (Prototrophic) (Part 3)

The operations and evaluations were carried out under the same conditions as in Example 3 except that the yeast HI003-1B strain prepared in Reference Example 1 was used. As a result, the transmembrane pressure difference became not less than 20 kPa at 500 hours and the culture was terminated. The result of the continuous fermentation test is shown in Table 6. As a result, it was revealed that lactic acid can be produced longer and more stably when polyploid yeast is used.

Comparative Example 5

Production of Lactic Acid by Continuous Fermentation Using Haploid Yeast (Prototrophic) (Part 4)

The operations and evaluations were carried out under the same conditions as in Example 4 except that the yeast HI003-1B strain prepared in Reference Example 1 was used. As a result, the transmembrane pressure difference became not less than 20 kPa at 500 hours and the culture was terminated. The result of the continuous fermentation test is shown in Table 6. As a result, it was revealed that lactic acid can be produced longer and more stably when polyploid yeast is used.

Comparative Example 6

Production of Lactic Acid by Continuous Fermentation Using Haploid Yeast (Auxotrophic) (Part 1)

The operations and evaluations were carried out under the same conditions as in Example 1 except that the yeast SU014-3B strain prepared in Reference Example 1 was used. As a result, the transmembrane pressure difference became not less than 20 kPa at 300 hours and the culture was terminated. The result of the continuous fermentation test is shown in Table 6. As a result, it was revealed that lactic acid can be produced longer and more stably when prototrophic yeast or polyploid yeast is used.

Comparative Example 7

Production of Lactic Acid by Continuous Fermentation Using Haploid Yeast (Auxotrophic) (Part 2)

The operations and evaluations were carried out under the same conditions as in Example 2 except that the yeast SU014-3B strain prepared in Reference Example 1 was used. As a result, the transmembrane pressure difference became not less than 20 kPa at 280 hours and the culture was terminated. The result of the continuous fermentation test is shown in Table 6. As a result, it was revealed that lactic acid can be produced longer and more stably when prototrophic yeast or polyploid yeast is used.

Comparative Example 8

Production of Lactic Acid by Continuous Fermentation Using Haploid Yeast (Auxotrophic) (Part 3)

The operations and evaluations were carried out under the same conditions as in Example 3 except that the yeast SU014-3B strain prepared in Reference Example 1 was used. As a result, the transmembrane pressure difference became not less than 20 kPa at 350 hours and the culture was terminated. The result of the continuous fermentation test is shown in Table 6. As a result, it was revealed that lactic acid can be produced longer and more stably when prototrophic yeast or polyploid yeast is used.

Comparative Example 9

Production of Lactic Acid by Continuous Fermentation Using Haploid Yeast (Auxotrophic) (Part 4)

The operations and evaluations were carried out under the same conditions as in

Example 4 except that the yeast SU014-3B strain prepared in Reference Example 1 was used. As a result, the transmembrane pressure difference became not less than 20 kPa at 270 hours and the culture was terminated. The result of the continuous fermentation test is shown in Table 6. As a result, it was revealed that lactic acid can be produced longer and more stably when prototrophic yeast or polyploid yeast is used.

Example 5

Production of Lactic Acid by Continuous Fermentation Using Polyploid (Prototrophic) Yeast Having Capacity to Produce Lactic Acid (Part 5)

The operations and evaluations were carried out under the same conditions as in Example 1 except that the lactic acid fermentation medium described in Table 4 was used. The result of 800 hours of a fermentation test is shown in Table 7. Even with the lactic acid fermentation medium having less nutrients than SC4 medium, stable production of lactic acid by continuous fermentation was possible by our method for producing lactic acid.

TABLE 4

| | |
|---|---|
| Raw sugar (manufactured by Muso Co., Ltd.) | 50 g |
| Ammonium sulfate | 1.5 g |
| | up to 1 L |

Example 6

Production of Lactic Acid by Continuous Fermentation Using Polyploid (Prototrophic) Yeast Having Capacity to Produce Lactic Acid (Part 6)

The operations and evaluations were carried out under the same conditions as in Example 2 except that the lactic acid fermentation medium described in Table 4 was used. The result of 800 hours of a fermentation test is shown in Table 7. Even with the lactic acid fermentation medium having less nutrients than SC4 medium, stable production of lactic acid by continuous fermentation was possible by our method for producing lactic acid.

Example 7

Production of Lactic Acid by Continuous Fermentation Using Polyploid (Prototrophic) Yeast Having Capacity to Produce Lactic Acid (Part 7)

The operations and evaluations were carried out under the same conditions as in Example 3 except that the lactic acid fermentation medium described in Table 4 was used. The result of 800 hours of a fermentation test is shown in Table 7. Even with the lactic acid fermentation medium having less nutrients than SC4 medium, stable production of lactic acid by continuous fermentation was possible by our method for producing lactic acid.

Example 8

Production of Lactic Acid by Continuous Fermentation Using Polyploid (Prototrophic) Yeast Having Capacity to Produce Lactic Acid (Part 8)

The operations and evaluations were carried out under the same conditions as in Example 4 except that the lactic acid fermentation medium described in Table 4 was used. The result of 800 hours of a fermentation test is shown in Table 7. Even with the lactic acid fermentation medium having less nutrients than SC4 medium, stable production of lactic acid by continuous fermentation was possible by our method for producing lactic acid.

Example 9

Production of Lactic Acid by Continuous Fermentation Using Polyploid Yeast (Auxotrophic) Having Capacity to Produce Lactic Acid (Part 1)

The operations and evaluations were carried out under the same conditions as in Example 5 except that the yeast SU014 strain prepared in Reference Example 1 was used. The result of 700 hours of a continuous fermentation test is shown in Table 7. Although the yield of lactic acid to saccharides and the rate of production of lactic acid were rather lower than in the cases of the prototrophic polyploid yeast, stable production of lactic acid by continuous fermentation was possible for a long time.

Example 10

Production of Lactic Acid by Continuous Fermentation Using Polyploid Yeast (Auxotrophic) Having Capacity to Produce Lactic Acid (Part 2)

The operations and evaluations were carried out under the same conditions as in Example 6 except that the yeast SU014 strain prepared in Reference Example 1 was used. The result of 700 hours of a fermentation test is shown in Table 7. Although the yield of lactic acid to saccharides and the rate of production of lactic acid were rather lower than in the cases of the prototrophic polyploid yeast, stable production of lactic acid by continuous fermentation was possible for a long time.

Example 11

Production of L-Lactic Acid by Continuous Fermentation Using Polyploid Yeast (Auxotrophic) Having Capacity to Produce Lactic Acid (Part 3)

The operations and evaluations were carried out under the same conditions as in Example 7 except that the yeast SU014 strain prepared in Reference Example 1 was used. The result of 650 hours of a continuous fermentation test is shown in Table 7. Although the yield of lactic acid to saccharides and the rate of production of lactic acid were rather lower than in the cases of the prototrophic polyploid yeast, stable production of lactic acid by continuous fermentation was possible for a long time.

Example 12

Production of Lactic Acid by Continuous Fermentation Using Polyploid Yeast (Auxotrophic) Having Capacity to Produce Lactic Acid (Part 4)

The operations and evaluations were carried out under the same conditions as in Example 8 except that the yeast SU014 strain prepared in Reference Example 1 was used. The result of 670 hours of a fermentation test is shown in Table 7. Although the yield of lactic acid to saccharides and the rate of production of lactic acid were rather lower than in the cases of the prototrophic polyploid yeast, stable production of lactic acid by continuous fermentation was possible for a long time.

Comparative Example 10

Production of Lactic Acid by Batch Fermentation Using Polyploid (Prototrophic) Yeast Having Capacity to Produce Lactic Acid The operations and evaluations were carried out under the same conditions as in Comparative Example 1 except that the lactic acid fermentation medium described in Table 4 was used. The result of batch fermentation is shown in Table 7. The fermentation time was short, and the yield of lactic acid to saccharides and the rate of production of lactic acid were inferior to those in the Examples.

Comparative Example 11

Production of Lactic Acid by Batch Fermentation Using Polyploid Yeast (Auxotrophic) Having Capacity to Produce Lactic Acid The operations and evaluations were carried out under the same conditions as in Comparative Example 2 except that the yeast SU014 strain prepared in Reference Example 1 was used. The result of batch fermentation is shown in Table 7. The fermentation time was short, and the yield of lactic acid to saccharides and the rate of production of lactic acid were inferior to those in the Examples.

Comparative Example 12

Production of Lactic Acid by Continuous Fermentation Using Haploid Yeast (Auxotrophic) Having Capacity to Produce Lactic Acid (Part 1)

The operations and evaluations were carried out under the same conditions as in Example 5 except that the yeast SU014-3B strain prepared in Reference Example 1 was used. As a result, the transmembrane pressure difference became not less than 20 kPa at 300 hours and the culture was terminated. The result of the continuous fermentation test is shown in Table 7. As a result, it was revealed that lactic acid can be produced longer and more stably when polyploid yeast is used.

Comparative Example 13

Production of Lactic Acid by Continuous Fermentation Using Haploid Yeast (Auxotrophic) Having Capacity to Produce Lactic Acid (Part 2)

The operations and evaluations were carried out in the same manner as in Example 6 except that the yeast SU014-3B strain prepared in Reference Example 1 was used. As a result, the transmembrane pressure difference became not less than 20 kPa at 280 hours and the culture was terminated. The result of the continuous fermentation test is shown in Table 7. As a result, it was revealed that lactic acid can be produced longer and more stably when polyploid yeast is used.

Comparative Example 14

Production of Lactic Acid by Continuous Fermentation Using Haploid Yeast (Auxotrophic) Having Capacity to Produce Lactic Acid (Part 3)

The operations and evaluations were carried out in the same manner as in Example 7 except that the yeast SU014-3B strain prepared in Reference Example 1 was used. As a result, in the case of the haploid yeast, the transmembrane pressure difference became not less than 20 kPa at 350 hours and the culture was terminated. The result of the continuous fermentation test is shown in Table 7. As a result, it was revealed that lactic acid can be produced longer and more stably when polyploid yeast is used.

Comparative Example 15

Production of Lactic Acid by Continuous Fermentation Using Haploid Yeast (Auxotrophic) Having Capacity to Produce Lactic Acid (Part 4)

The operations and evaluations were carried out in the same manner as in Example 8 except that the yeast SU014-3B strain prepared in Reference Example 1 was used. As a result, the transmembrane pressure difference became not less than 20 kPa at 270 hours and the culture was terminated. The result of the continuous fermentation test is shown in Table 7. As a result, it was revealed that lactic acid can be produced longer and more stably when polyploid yeast is used.

Example 13

Production of Lactic Acid by Continuous Fermentation Using Polyploid (Prototrophic) Yeast Having Capacity to Produce Lactic Acid (Part 9)

Figure 6:
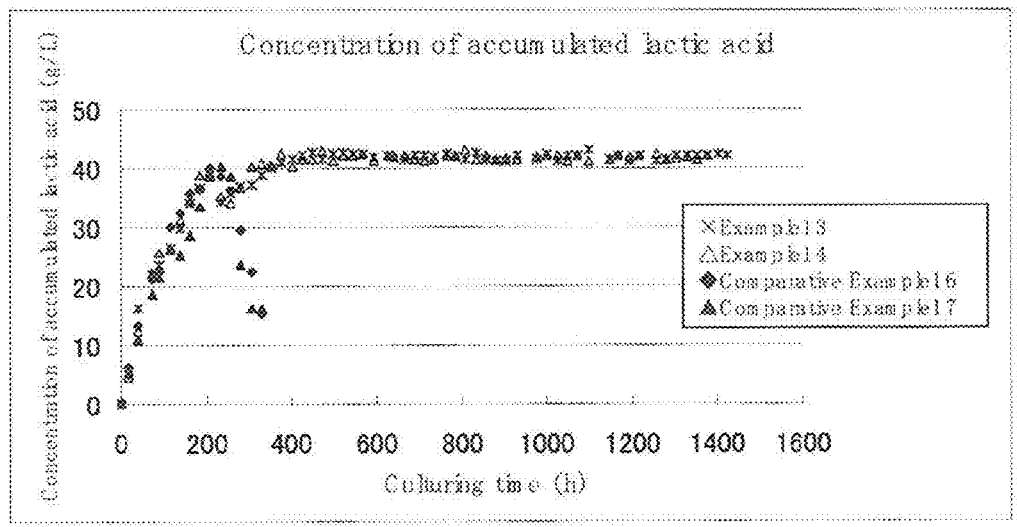
FIG. 6 shows changes in the concentrations of accumulated lactic acid in Examples 13 and 14 and Comparative Examples 16 and 17.
Figure 7:
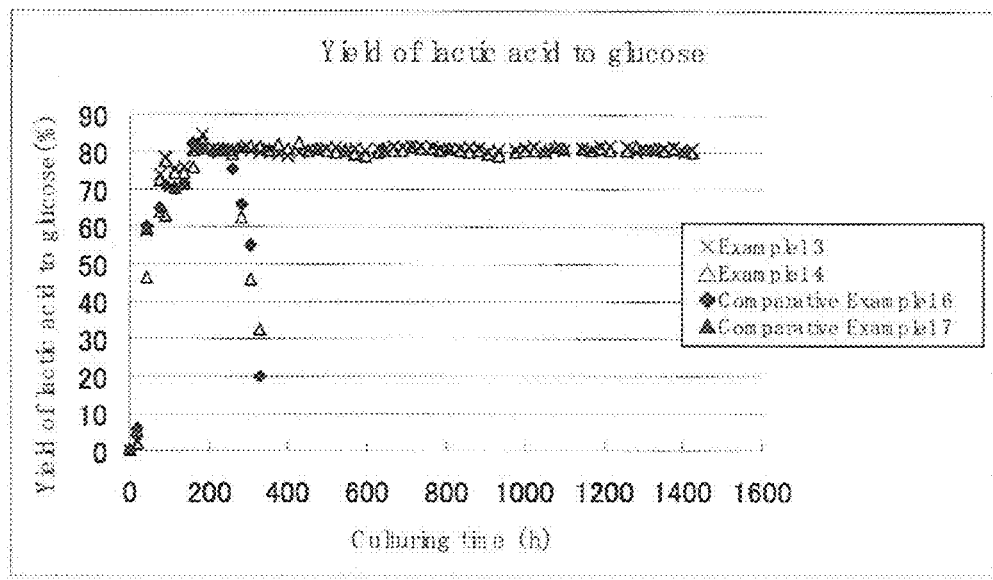
FIG. 7 shows changes in the yields of lactic acid to glucose in Examples 13 and 14 and Comparative Examples 16 and 17.
Figure 8:
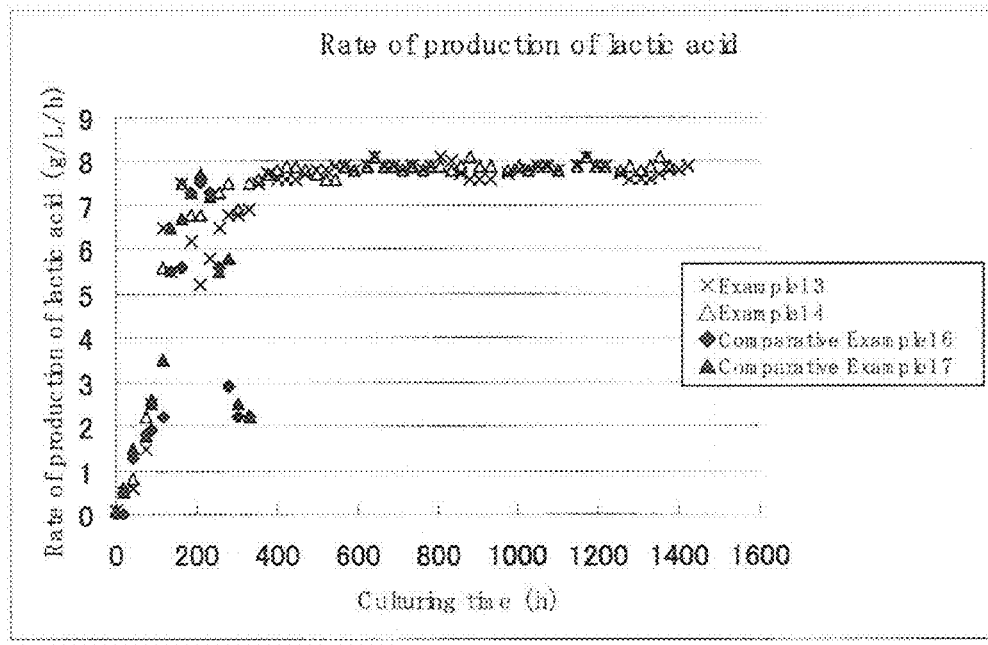
FIG. 8 shows changes in the rates of production of lactic acid in Examples 13 and 14 and Comparative Examples 16 and 17.

The operations and evaluations were carried out under the same conditions as in Example 1 except that the effective filtration area of the membrane separation element was increased to 240 cm$^2$ and the lactic acid fermentation medium 2 described in Table 5 was used. The results of 1400 hours of a fermentation test are shown in FIGS. 6 to 8. Stable production of lactic acid by continuous fermentation was possible for a long time by our method for producing lactic acid.

TABLE 5

| | |
|---|---|
| Raw sugar (manufactured by Muso Co., Ltd.) | 100 g |
| Ammonium sulfate | 1.5 g |
| | up to 1 L |

Example 14

Production of Lactic Acid by Continuous Fermentation Using Polyploid (Prototrophic) Yeast Having Capacity to Produce Lactic Acid (Part 10)

The operations and evaluations were carried out under the same conditions as in Example 3 except that the effective filtration area of the membrane separation element was increased to 240 cm² and the lactic acid fermentation medium 2 described in Table 5 was used. The results of 1350 hours of a fermentation test are shown in FIGS. 6 to 8. Stable production of lactic acid by continuous fermentation was possible for a long time by our method for producing lactic acid.

Example 15

Production of Lactic Acid by Continuous Fermentation Using Polyploid (Prototrophic) Yeast Having Capacity to Produce Lactic Acid (Part 11)

Figure 9:
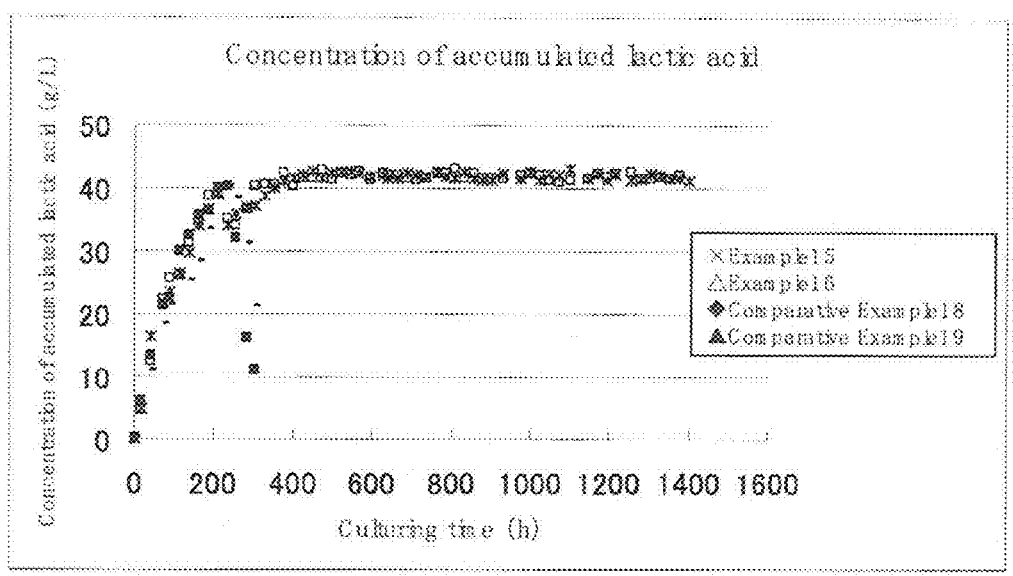
FIG. 9 shows changes in the concentrations of accumulated lactic acid in Examples 15 and 16 and Comparative Examples 18 and 19.
Figure 10:
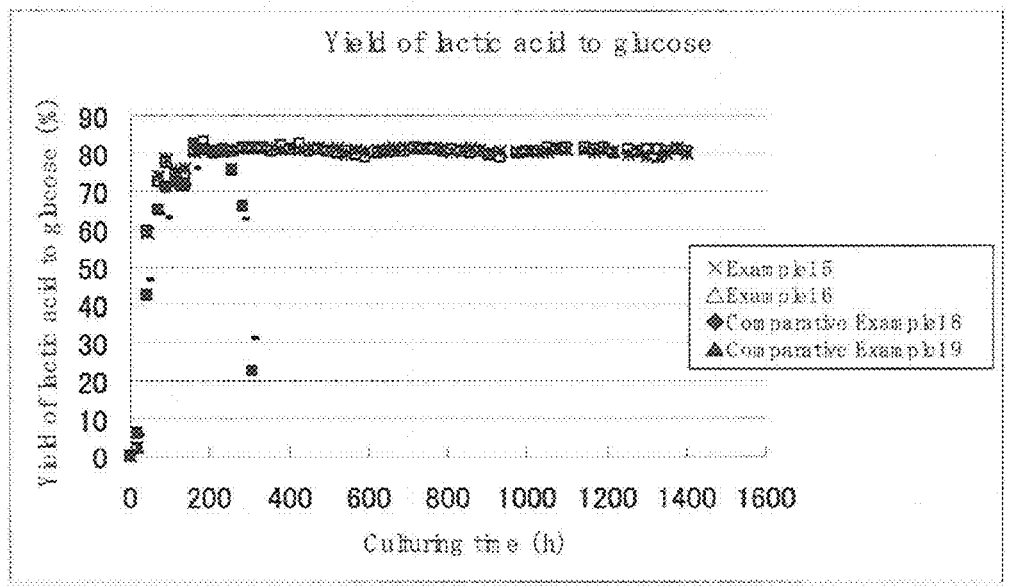
FIG. 10 shows changes in the yields of lactic acid to glucose in Examples 15 and 16 and Comparative Examples 18 and 19.
Figure 11:
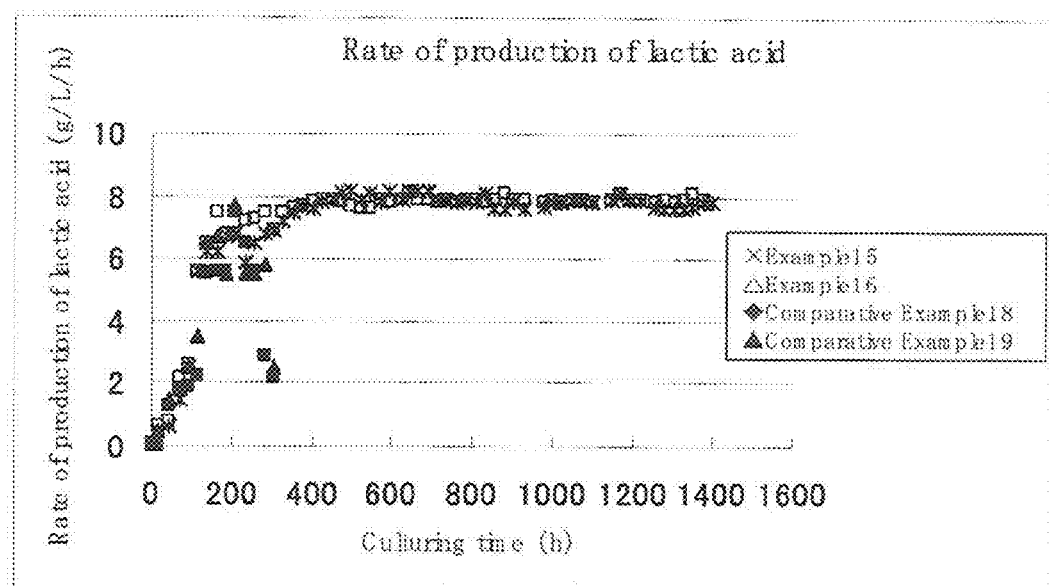
FIG. 11 shows changes in the rates of production of lactic acid in Examples 15 and 16 and Comparative Examples 18 and 19.

The operations and evaluations were carried out under the same conditions as in Example 13 except that the yeast SE001 strain prepared in Reference Example 1 was used. The results of 1350 hours of a fermentation test are shown in FIGS. 9 to 11. Stable production of lactic acid by continuous fermentation was possible for a long time by our method for producing lactic acid.

Example 16

Production of Lactic Acid by Continuous Fermentation Using Polyploid (Prototrophic) Yeast Having Capacity to Produce Lactic Acid (Part 12)

The operations and evaluations were carried out under the same conditions as in Example 14 except that the yeast SE001 strain prepared in Reference Example 1 was used. The results of 1350 hours of a fermentation test are shown in FIGS. 9 to 11. Stable production of lactic acid by continuous fermentation was possible for a long time by our method for producing lactic acid.

Comparative Example 16

Production of Lactic Acid by Continuous Fermentation Using Haploid Yeast (Auxotrophic) Having Capacity to Produce Lactic Acid (Part 5)

The operations and evaluations were carried out under the same conditions as in Example 13 except that the yeast SU014-3B strain prepared in Reference Example 1 was used. As a result, the transmembrane pressure difference became not less than 20 kPa at 300 hours and the culture was terminated. The results of the continuous fermentation test are shown in FIGS. 9 to 11. As a result, it was revealed that lactic acid can be produced longer and more stably when polyploid yeast is used.

Comparative Example 17

Production of Lactic Acid by Continuous Fermentation Using Haploid Yeast (Auxotrophic) Having Capacity to Produce Lactic Acid (Part 6)

The operations and evaluations were carried out under the same conditions as in Example 14 except that the yeast SU014-3B strain prepared in Reference Example 1 was used. As a result, the transmembrane pressure difference became not less than 20 kPa at 280 hours and the culture was terminated. The results of the continuous fermentation test are shown in FIGS. 9 to 11. As a result, it was revealed that lactic acid can be produced longer and more stably when polyploid yeast is used.

Comparative Example 18

Production of Lactic Acid by Continuous Fermentation Using Haploid Yeast (Auxotrophic) Having Capacity to Produce Lactic Acid (Part 7)

The operations and evaluations were carried out under the same conditions as in Example 15 except that the yeast SE001-1A strain prepared in Reference Example 1 was used. As a result, the transmembrane pressure difference became not less than 20 kPa at 300 hours and the culture was terminated. The results of the continuous fermentation test are shown in FIGS. 9 to 11. As a result, it was revealed that lactic acid can be produced longer and more stably when polyploid yeast is used.

Comparative Example 19

Production of Lactic Acid by Continuous Fermentation Using Haploid Yeast (Auxotrophic) Having Capacity to Produce Lactic Acid (Part 8)

The operations and evaluations were carried out under the same conditions as in Example 16 except that the yeast SE001-1A strain prepared in Reference Example 1 was used. As a result, the transmembrane pressure difference became not less than 20 kPa at 270 hours and the culture was terminated. The results of the continuous fermentation test are shown in FIGS. 9 to 11. As a result, it was revealed that lactic acid can be produced longer and more stably when polyploid yeast is used.

The culture conditions in Examples 1 to 16 and Comparative Examples 1 to 19 are shown in Table 8.

TABLE 6

|  | Example 1 | Example 2 | Example 3 | Example 4 | Comparative Example 1 | Comparative Example 2 | Comparative Example 3 |
|---|---|---|---|---|---|---|---|
| Fermentation time (hr.) | 800 | 800 | 750 | 770 | 72 | 600 | 600 |
| Total glucose fed | 8424 | 7896 | 6653 | 7500 | 100 | 6312 | 5922 |
| Total L-lactic acid produced (g) | 5882 | 5764 | 4790 | 5600 | 26 | 4366 | 4323 |
| Unused glucose | 20 | 10 | 20 | 10 | 0 | 20 | 10 |
| Yield of L-lactic acid to glucose | 0.7 | 0.73 | 0.72 | 0.75 | 0.22 | 0.65 | 0.67 |

TABLE 6-continued

| | | | | | | | |
|---|---|---|---|---|---|---|---|
| Rate of production of L-lactic acid (g/L/hr.) | 3.7 | 4.8 | 3.2 | 4.8 | 0.36 | 3.5 | 4.6 |

| | Comparative Example 4 | Comparative Example 5 | Comparative Example 6 | Comparative Example 7 | Comparative Example 8 | Comparative Example 9 |
|---|---|---|---|---|---|---|
| Fermentation time (hr.) | 500 | 500 | 300 | 280 | 350 | 270 |
| Total glucose fed | 4158 | 4687 | 3240 | 2820 | 3000 | 2420 |
| Total L-lactic acid produced (g) | 2993 | 3857 | 1920 | 1700 | 1770 | 1488 |
| Unused glucose | 20 | 10 | 40 | 70 | 40 | 20 |
| Yield of L-lactic acid to glucose | 0.66 | 0.68 | 0.6 | 0.62 | 0.59 | 0.62 |
| Rate of production of L-lactic acid (g/L/hr.) | 3 | 4.5 | 3.2 | 4 | 2.5 | 3.8 |

TABLE 7

| | Example 5 | Example 6 | Example 7 | Example 8 | Example 9 | Example 10 | Example 11 | Example 12 |
|---|---|---|---|---|---|---|---|---|
| Fermentation time (hr.) | 800 | 800 | 750 | 770 | 700 | 700 | 650 | 670 |
| Total glucose fed | 6362 | 10530 | 5020 | 9876 | 5610 | 8057 | 4170 | 8283 |
| Total L-lactic acid produced (g) | 4440 | 7680 | 3600 | 7392 | 3360 | 4900 | 2535 | 4958 |
| Unused glucose | 20 | 10 | 20 | 20 | 10 | 25 | 15 | 20 |
| Yield of L-lactic acid to glucose | 0.7 | 0.73 | 0.72 | 0.75 | 0.6 | 0.61 | 0.61 | 0.6 |
| Rate of production of L-lactic acid (g/L/hr.) | 3.7 | 4.8 | 3.2 | 4.8 | 3.2 | 3.5 | 2.6 | 3.7 |

| | Comparative Example 10 | Comparative Example 11 | Comparative Example 12 | Comparative Example 13 | Comparative Example 14 | Comparative Example 15 |
|---|---|---|---|---|---|---|
| Fermentation time (hr.) | 72 | 70 | 300 | 280 | 350 | 270 |
| Total glucose fed | 100 | 100 | 2354 | 3586 | 2302 | 3295 |
| Total L-lactic acid produced (g) | 26 | 22 | 1350 | 2128 | 1312 | 1998 |
| Unused glucose | 0 | 0 | 27 | 40 | 40 | 20 |
| Yield of L-lactic acid to glucose | 0.26 | 0.22 | 0.58 | 0.6 | 0.58 | 0.61 |
| Rate of production of L-lactic acid (g/L/hr.) | 0.36 | 0.32 | 3 | 3.8 | 2.5 | 3.7 |

TABLE 8

| | Yeast Sample | Culture apparatus | Separation membrane | Culture medium | Result | Area of separation membrane |
|---|---|---|---|---|---|---|
| Example 1 | HI003 | FIG. 1 | Reference Example 3 | Table 3 | Table 6 | 60 cm$^2$ |
| Example 2 | HI003 | FIG. 2 | Reference Example 3 | Table 3 | Table 6 | 120 cm$^2$ |
| Example 3 | HI003 | FIG. 1 | Reference Example 4 | Table 3 | Table 6 | 60 cm$^2$ |
| Example 4 | HI003 | FIG. 2 | Reference Example 4 | Table 3 | Table 6 | 120 cm$^2$ |
| Example 5 | HI003 | FIG. 1 | Reference Example 3 | Table 4 | Table 7 | 60 cm$^2$ |
| Example 6 | HI003 | FIG. 2 | Reference Example 3 | Table 4 | Table 7 | 120 cm$^2$ |
| Example 7 | HI003 | FIG. 1 | Reference Example 4 | Table 4 | Table 7 | 60 cm$^2$ |
| Example 8 | HI003 | FIG. 2 | Reference Example 4 | Table 4 | Table 7 | 120 cm$^2$ |
| Example 9 | SU014 | FIG. 1 | Reference Example 3 | Table 4 | Table 7 | 60 cm$^2$ |
| Example 10 | SU014 | FIG. 2 | Reference Example 3 | Table 4 | Table 7 | 120 cm$^2$ |
| Example 11 | SU014 | FIG. 1 | Reference Example 4 | Table 4 | Table 7 | 60 cm$^2$ |
| Example 12 | SU014 | FIG. 2 | Reference Example 4 | Table 4 | Table 7 | 120 cm$^2$ |
| Example 13 | HI003 | FIG. 1 | Reference Example 3 | Table 5 | FIG. 6, FIG. 7, FIG. 8 | 240 cm$^2$ |
| Example 14 | HI003 | FIG. 1 | Reference Example 4 | Table 5 | FIG. 6, FIG. 7, FIG. 8 | 240 cm$^2$ |
| Example 15 | SE001 | FIG. 1 | Reference Example 5 | Table 5 | FIG. 9, FIG. 10, FIG. 11 | 240 cm$^2$ |
| Example 16 | SE001 | FIG. 1 | Reference Example 6 | Table 5 | FIG. 9, FIG. 10, FIG. 11 | 240 cm$^2$ |
| Comparative Example 1 | HI003 | FIG. 1 (Batch Culture) | | Table 3 | Table 6 | |
| Comparative Example 2 | HI003-1B | FIG. 1 | Reference Example 3 | Table 3 | Table 6 | 60 cm$^2$ |
| Comparative Example 3 | HI003-1B | FIG. 2 | Reference Example 3 | Table 3 | Table 6 | 120 cm$^2$ |
| Comparative Example 4 | HI003-1B | FIG. 1 | Reference Example 4 | Table 3 | Table 6 | 60 cm$^2$ |
| Comparative Example 5 | HI003-1B | FIG. 2 | Reference Example 4 | Table 3 | Table 6 | 120 cm$^2$ |
| Comparative Example 6 | SU014-3B | FIG. 1 | Reference Example 3 | Table 3 | Table 6 | 60 cm$^2$ |
| Comparative Example 7 | SU014-3B | FIG. 2 | Reference Example 3 | Table 3 | Table 6 | 120 cm$^2$ |
| Comparative Example 8 | SU014-3B | FIG. 1 | Reference Example 4 | Table 3 | Table 6 | 60 cm$^2$ |
| Comparative Example 9 | SU014-3B | FIG. 2 | Reference Example 4 | Table 3 | Table 6 | 120 cm$^2$ |
| Comparative Example 10 | HI003 | FIG. 1 (Batch Culture) | | Table 4 | Table 7 | |
| Comparative Example 11 | SU014 | FIG. 1 (Batch Culture) | | Table 4 | Table 7 | |
| Comparative Example 12 | SU014-3B | FIG. 1 | Reference Example 3 | Table 4 | Table 7 | 60 cm$^2$ |
| Comparative Example 13 | SU014-3B | FIG. 2 | Reference Example 3 | Table 4 | Table 7 | 120 cm$^2$ |
| Comparative Example 14 | SU014-3B | FIG. 1 | Reference Example 4 | Table 4 | Table 7 | 60 cm$^2$ |
| Comparative Example 15 | SU014-3B | FIG. 2 | Reference Example 4 | Table 4 | Table 7 | 120 cm$^2$ |
| Comparative Example 16 | SU014-3B | FIG. 1 | Reference Example 3 | Table 5 | FIG. 6, FIG. 7, FIG. 8 | 240 cm$^2$ |
| Comparative Example 17 | SU014-3B | FIG. 1 | Reference Example 4 | Table 5 | FIG. 6, FIG. 7, FIG. 8 | 240 cm$^2$ |
| Comparative Example 18 | SE001-1A | FIG. 1 | Reference Example 5 | Table 5 | FIG. 9, FIG. 10, FIG. 11 | 240 cm$^2$ |
| Comparative Example 19 | SE001-1A | FIG. 1 | Reference Example 6 | Table 5 | FIG. 9, FIG. 10, FIG. 11 | 240 cm$^2$ |

INDUSTRIAL APPLICABILITY

By our methods for producing lactic acid by continuous fermentation using polyploid yeast as the yeast sample, continuous fermentation wherein a high productivity of lactic acid which is the desired fermentation product can be stably maintained for a long time is possible under simple operating conditions. Therefore, lactic acid as a fermentation product can be stably produced at a low cost widely in the fermentation industry.

The invention claimed is:

1. A method of producing lactic acid by continuous fermentation comprising:
   filtering a culture of polyploid prototrophic yeast having a capacity to produce lactic acid by introduction of a lactate dehydrogenase gene through a porous membrane having an average pore size of not less than 0.01 μm and less than 1 μm; and
   recovering the lactic acid from the filtrate while the unfiltered liquid is retained in or returned to the culture and a fermentation feedstock is added to the culture wherein said filtration is carried out with a transmembrane pressure difference of said porous membrane within a range of 0.1 kPa to less than 20 kPa and wherein said continuous fermentation is continued for not less than 400 hours.

2. The method according to claim 1, wherein said polyploid prototrophic yeast is diploid.

3. The method according to claim 1, wherein the yield of lactic acid to saccharides in said continuous fermentation is not less than 70%.

4. The method according to claim 1, wherein the concentration of accumulated lactic acid in the culture subjected to said continuous fermentation is not less than 40 g/L.

5. The method according to claim 1, wherein a rate of production of lactic acid during said continuous fermentation is not less than 7.5 g/L/h.

6. The method according to claim 1, wherein said polyploid prototrophic yeast belongs to *Saccharomyces*.

7. The method according to claim 1, wherein said polyploid prototrophic yeast is *Saccharomyces cerevisiae*.

* * * * *